(12) United States Patent
Garraway et al.

(10) Patent No.: US 8,637,246 B2
(45) Date of Patent: Jan. 28, 2014

(54) BRAF MUTATIONS CONFERRING RESISTANCE TO BRAF INHIBITORS

(75) Inventors: Levi Garraway, Newton, MA (US); Caroline Emery, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 13/580,651

(22) PCT Filed: Feb. 22, 2011

(86) PCT No.: PCT/US2011/025645
§ 371 (c)(1),
(2), (4) Date: Aug. 22, 2012

(87) PCT Pub. No.: WO2011/106298
PCT Pub. Date: Sep. 1, 2011

(65) Prior Publication Data
US 2013/0004509 A1    Jan. 3, 2013

Related U.S. Application Data

(60) Provisional application No. 61/308,275, filed on Feb. 25, 2010.

(51) Int. Cl.
C12Q 1/00      (2006.01)
A61P 35/00     (2006.01)

(52) U.S. Cl.
USPC ......................... 435/6.11; 514/19.3

(58) Field of Classification Search
None
See application file for complete search history.

(56) References Cited

U.S. PATENT DOCUMENTS

| | | |
|---|---|---|
| 4,582,788 A | 4/1986 | Erlich |
| 4,656,127 A | 4/1987 | Mundy |
| 4,659,774 A | 4/1987 | Webb et al. |
| 4,682,195 A | 7/1987 | Yilmaz |
| 4,683,194 A | 7/1987 | Saiki et al. |
| 4,683,202 A | 7/1987 | Mullis |
| 4,684,611 A | 8/1987 | Schilperoort et al. |
| 4,816,571 A | 3/1989 | Andrus et al. |
| 4,879,236 A | 11/1989 | Smith et al. |
| 4,946,773 A | 8/1990 | Maniatis et al. |
| 4,952,500 A | 8/1990 | Finnerty et al. |
| 4,959,463 A | 9/1990 | Froehler et al. |
| 5,096,676 A | 3/1992 | McPherson et al. |
| 5,141,813 A | 8/1992 | Nelson |
| 5,223,409 A | 6/1993 | Ladner et al. |
| 5,264,566 A | 11/1993 | Froehler et al. |
| 5,302,523 A | 4/1994 | Coffee et al. |
| 5,322,783 A | 6/1994 | Tomes et al. |
| 5,384,253 A | 1/1995 | Krzyzek et al. |
| 5,419,278 A | 5/1995 | Carter |
| 5,428,148 A | 6/1995 | Reddy et al. |
| 5,464,765 A | 11/1995 | Coffee et al. |
| 5,538,877 A | 7/1996 | Lundquist et al. |
| 5,538,880 A | 7/1996 | Lundquist et al. |
| 5,550,318 A | 8/1996 | Adams et al. |
| 5,554,744 A | 9/1996 | Bhongle et al. |
| 5,563,055 A | 10/1996 | Townsend et al. |
| 5,574,146 A | 11/1996 | Reddy et al. |
| 5,580,859 A | 12/1996 | Felgner et al. |
| 5,589,466 A | 12/1996 | Felgner et al. |
| 5,591,616 A | 1/1997 | Hiei et al. |
| 5,602,244 A | 2/1997 | Caruthers et al. |
| 5,610,042 A | 3/1997 | Chang et al. |
| 5,645,897 A | 7/1997 | Andra |
| 5,650,298 A | 7/1997 | Bujard et al. |
| 5,656,610 A | 8/1997 | Shuler et al. |
| 5,702,932 A | 12/1997 | Hoy et al. |
| 5,705,629 A | 1/1998 | Bhongle |
| 5,736,524 A | 4/1998 | Content et al. |
| 5,780,448 A | 7/1998 | Davis |
| 5,789,215 A | 8/1998 | Berns et al. |
| 5,849,483 A | 12/1998 | Shuber |
| 5,851,770 A | 12/1998 | Babon et al. |
| 5,866,337 A | 2/1999 | Schon |
| 5,871,986 A | 2/1999 | Boyce |
| 5,925,525 A | 7/1999 | Fodor et al. |
| 5,928,870 A | 7/1999 | Lapidus et al. |
| 5,945,100 A | 8/1999 | Fick |
| 5,952,174 A | 9/1999 | Nikiforov et al. |
| 5,981,274 A | 11/1999 | Tyrrell et al. |
| 5,994,624 A | 11/1999 | Trolinder et al. |
| 6,054,273 A | 4/2000 | Housman |
| 6,200,754 B1 | 3/2001 | Housman et al. |
| 6,296,673 B1 | 10/2001 | Santarsiero et al. |
| 6,310,060 B1 | 10/2001 | Barrett et al. |
| 6,440,966 B1 | 8/2002 | Barrett et al. |

(Continued)

FOREIGN PATENT DOCUMENTS

| | | |
|---|---|---|
| AT | 404556 B | 12/1998 |
| AT | 277895 T | 10/2004 |

(Continued)

OTHER PUBLICATIONS

Board et al., Detection of BRAF mutations in the tumour and serum of patients enrolled in the AZD6244 (ARRY-142886) advanced melanoma phase II study, Brit. J. Cancer, 101, 1724-1730, 2009.*

(Continued)

*Primary Examiner* — Elly-Gerald Stoica
(74) *Attorney, Agent, or Firm* — Brinks Gilson & Lione

(57) ABSTRACT

The present invention relates to methods, compositions and kits concerning resistance to treatment with an anti-cancer agent, specifically an inhibitor of BRAF. In particular embodiments, the invention concerns mutations in a BRAF sequence that confer resistance to a BRAF inhibitor. Identification of such mutations in a BRAF sequence allows the identification and design of second-generation BRAF inhibitors. Methods and kits for detecting the presence of a mutant BRAF sequence in a sample are also provided.

8 Claims, 8 Drawing Sheets

(56) References Cited

U.S. PATENT DOCUMENTS

| | | |
|---|---|---|
| 6,455,582 B1 | 9/2002 | Tecle |
| 6,469,004 B1 | 10/2002 | Barrett et al. |
| 6,492,363 B2 | 12/2002 | Barrett et al. |
| 6,506,798 B1 | 1/2003 | Barrett et al. |
| 6,545,030 B1 | 4/2003 | Barrett et al. |
| 6,750,217 B2 | 6/2004 | Barrett et al. |
| 6,770,778 B2 | 8/2004 | Barrett et al. |
| 6,821,963 B2 | 11/2004 | Barrett et al. |
| 6,835,749 B2 | 12/2004 | Tecle |
| 6,891,066 B2 | 5/2005 | Rewcastle et al. |
| 6,960,614 B2 | 11/2005 | Barrett et al. |
| 6,989,451 B2 | 1/2006 | Zhang et al. |
| 7,019,033 B2 | 3/2006 | Barrett et al. |
| 7,078,438 B2 | 7/2006 | Rewcastle et al. |
| 7,144,907 B2 | 12/2006 | Wallace et al. |
| 7,160,915 B2 | 1/2007 | Barrett et al. |
| 7,169,816 B2 | 1/2007 | Barrett et al. |
| 7,173,136 B2 | 2/2007 | Hennequin |
| 7,230,099 B2 | 6/2007 | Wallace et al. |
| 7,232,826 B2 | 6/2007 | Velaparthi et al. |
| 7,253,199 B2 | 8/2007 | Arkinstall et al. |
| 7,271,178 B2 | 9/2007 | Wallace et al. |
| 7,273,877 B2 | 9/2007 | Black et al. |
| 7,307,071 B2 | 12/2007 | Lyons et al. |
| 7,371,869 B2 | 5/2008 | Goodnow, Jr. et al. |
| 7,378,423 B2 | 5/2008 | Kawasaki et al. |
| 7,411,001 B2 | 8/2008 | Barrett et al. |
| 7,442,507 B2 * | 10/2008 | Polsky et al. ............... 435/6.14 |
| 2002/0022647 A1 | 2/2002 | Barrett et al. |
| 2003/0004193 A1 | 1/2003 | Barrett et al. |
| 2003/0045521 A1 | 3/2003 | Tecle |
| 2003/0078428 A1 | 4/2003 | Barrett et al. |
| 2003/0092748 A1 | 5/2003 | Barrett et al. |
| 2003/0125359 A1 | 7/2003 | Lyons et al. |
| 2003/0149015 A1 | 8/2003 | Barrett et al. |
| 2003/0216460 A1 | 11/2003 | Wallace et al. |
| 2003/0232889 A1 | 12/2003 | Barrett et al. |
| 2004/0006245 A1 | 1/2004 | Rewcastle et al. |
| 2004/0039037 A1 | 2/2004 | Zhang et al. |
| 2004/0054172 A1 | 3/2004 | Barrett et al. |
| 2004/0092514 A1 | 5/2004 | Velaparthi et al. |
| 2004/0171632 A1 | 9/2004 | Gowan et al. |
| 2005/0004186 A1 | 1/2005 | Barrett et al. |
| 2005/0026964 A1 | 2/2005 | Black et al. |
| 2005/0026970 A1 | 2/2005 | Barrett et al. |
| 2005/0049276 A1 | 3/2005 | Kaufman et al. |
| 2005/0049419 A1 | 3/2005 | Wallace et al. |
| 2005/0049429 A1 | 3/2005 | Barrett et al. |
| 2005/0054701 A1 | 3/2005 | Wallace et al. |
| 2005/0054706 A1 | 3/2005 | Arkinstall et al. |
| 2005/0059710 A1 | 3/2005 | Barrett et al. |
| 2005/0130943 A1 | 6/2005 | Wallace et al. |
| 2005/0130976 A1 | 6/2005 | Wallace et al. |
| 2005/0137263 A1 | 6/2005 | Rewcastle et al. |
| 2005/0153942 A1 | 7/2005 | Wallace et al. |
| 2005/0176820 A1 | 8/2005 | Barrett et al. |
| 2005/0187247 A1 | 8/2005 | Berger et al. |
| 2005/0250782 A1 | 11/2005 | Marlow et al. |
| 2005/0256123 A1 | 11/2005 | Marlow et al. |
| 2005/0282856 A1 | 12/2005 | Hennequin |
| 2006/0014768 A1 | 1/2006 | Kawasaki et al. |
| 2006/0030610 A1 | 2/2006 | Koch et al. |
| 2006/0041146 A1 | 2/2006 | Chu et al. |
| 2006/0052608 A1 | 3/2006 | Barrett et al. |
| 2006/0063814 A1 | 3/2006 | Goodnow, Jr. et al. |
| 2006/0079526 A1 | 4/2006 | Wrasidlo et al. |
| 2006/0106225 A1 | 5/2006 | Wallace et al. |
| 2006/0189649 A1 | 8/2006 | Wallace et al. |
| 2006/0189668 A1 | 8/2006 | Wallace et al. |
| 2006/0189808 A1 | 8/2006 | Wallace et al. |
| 2006/0194802 A1 | 8/2006 | Abdellaoui et al. |
| 2006/0270643 A1 | 11/2006 | Chang et al. |
| 2007/0049591 A1 | 3/2007 | Pinkerton et al. |
| 2007/0105859 A1 | 5/2007 | Isshiki et al. |
| 2007/0112038 A1 | 5/2007 | Marlow et al. |
| 2007/0191346 A1 | 8/2007 | Hennequin |
| 2007/0197617 A1 | 8/2007 | Chen et al. |
| 2007/0238710 A1 | 10/2007 | Yan et al. |
| 2007/0244164 A1 | 10/2007 | Yan et al. |
| 2007/0287709 A1 | 12/2007 | Goutopoulos et al. |
| 2007/0287737 A1 | 12/2007 | Goutopoulos et al. |
| 2007/0293544 A1 | 12/2007 | Abel et al. |
| 2007/0293555 A1 | 12/2007 | Arkinstall et al. |
| 2007/0299103 A1 | 12/2007 | Abel et al. |
| 2008/0058340 A1 | 3/2008 | Maderna et al. |
| 2008/0081821 A1 | 4/2008 | Savy et al. |
| 2008/0085886 A1 | 4/2008 | Savy et al. |
| 2008/0166359 A1 | 7/2008 | Lamb |
| 2008/0188453 A1 | 8/2008 | Adams et al. |

FOREIGN PATENT DOCUMENTS

| | | |
|---|---|---|
| AT | 302193 T | 9/2005 |
| AT | 302761 T | 9/2005 |
| AT | 309205 T | 11/2005 |
| AT | 310567 T | 12/2005 |
| AT | 311363 T | 12/2005 |
| AT | 344791 T | 11/2006 |
| AT | 383360 T | 1/2008 |
| AU | 2001273498 B2 | 1/2002 |
| AU | 757046 B2 | 1/2003 |
| AU | 2002359291 B2 | 5/2003 |
| AU | 2002347360 A1 | 6/2003 |
| AU | 2002365665 A1 | 6/2003 |
| AU | 2002365899 B2 | 6/2003 |
| AU | 2003220202 A1 | 9/2003 |
| AU | 756586 C | 1/2004 |
| AU | 2003275282 A1 | 4/2004 |
| AU | 2003278369 A1 | 6/2004 |
| AU | 2003287366 A8 | 6/2004 |
| AU | 2003291268 A1 | 6/2004 |
| AU | 2003286306 A1 | 7/2004 |
| AU | 2004270699 A1 | 3/2005 |
| AU | 2004293018 A1 | 6/2005 |
| AU | 2004293019 A1 | 6/2005 |
| AU | 2005252110 B2 | 12/2005 |
| AU | 2005265769 A1 | 2/2006 |
| AU | 2005274390 A1 | 2/2006 |
| AU | 2005276974 A1 | 3/2006 |
| AU | 2005284293 A1 | 3/2006 |
| AU | 2005298932 A1 | 5/2006 |
| AU | 2005311451 A1 | 6/2006 |
| AU | 2006272837 A1 | 2/2007 |
| AU | 2006299902 A1 | 4/2007 |
| AU | 2006302415 A1 | 4/2007 |
| AU | 2008202731 A1 | 7/2008 |
| BR | 0317254 | 11/2005 |
| BR | 0412851 | 10/2006 |
| BR | 0414111 | 10/2006 |
| BR | 0416692 | 1/2007 |
| BR | 0511967 | 1/2008 |
| BR | 0513750 | 5/2008 |
| BR | 0514515 | 6/2008 |
| BR | 0515371 | 7/2008 |
| CA | 2 290 506 A1 | 1/1999 |
| CA | 2 290 509 A1 | 1/1999 |
| CA | 2 352 326 A1 | 6/2000 |
| CA | 2 349 467 A1 | 7/2000 |
| CA | 2 349 832 A1 | 7/2000 |
| CA | 2 355 374 A1 | 7/2000 |
| CA | 2 355 470 A1 | 7/2000 |
| CA | 2 416 685 A1 | 1/2002 |
| CA | 2 463 101 A1 | 5/2003 |
| CA | 2 466 762 A1 | 6/2003 |
| CA | 2 472 367 A1 | 7/2003 |
| CA | 2 473 545 A1 | 7/2003 |
| CA | 2 478 534 A1 | 9/2003 |
| CA | 2 509 405 A1 | 7/2004 |
| CA | 2 532 067 A1 | 2/2005 |
| CA | 2 537 321 A1 | 3/2005 |
| CA | 2 545 660 A1 | 6/2005 |
| CA | 2 546 353 A1 | 6/2005 |
| CA | 2 569 850 A1 | 12/2005 |
| CA | 2 575 232 A1 | 2/2006 |

(56) References Cited

FOREIGN PATENT DOCUMENTS

| | | |
|---|---|---|
| CA | 2 576 599 A1 | 2/2006 |
| CA | 2 578 283 A1 | 3/2006 |
| CA | 2 579 130 A1 | 3/2006 |
| CA | 2 582 247 A1 | 5/2006 |
| CA | 2 586 796 A1 | 6/2006 |
| CA | 2 587 178 A1 | 6/2006 |
| CA | 2 618 218 A1 | 2/2007 |
| CA | 2 608 201 A1 | 4/2007 |
| CA | 2 622 755 A1 | 4/2007 |
| CN | 1652792 A | 8/2005 |
| CN | 1874769 A | 12/2006 |
| CN | 1905873 A | 1/2007 |
| CN | 101006085 A | 7/2007 |
| CN | 101006086 A | 7/2007 |
| CN | 101023079 A | 8/2007 |
| CN | 101044125 A | 9/2007 |
| CN | 101065358 A | 10/2007 |
| CN | 101124199 A | 2/2008 |
| EE | 200100339 A | 10/2002 |
| EE | 200100373 A | 10/2002 |
| EE | 200100374 A | 12/2002 |
| EE | 200300030 A | 10/2004 |
| EP | 0 050 424 A1 | 4/1982 |
| EP | 0 084 796 B1 | 8/1983 |
| EP | 0 201 184 A2 | 12/1986 |
| EP | 0 237 362 A1 | 9/1987 |
| EP | 0 266 032 A1 | 5/1988 |
| EP | 1 438 295 A2 | 7/2004 |
| EP | 0 993 439 B1 | 9/2004 |
| EP | 1 467 965 A2 | 10/2004 |
| EP | 1 467 968 A2 | 10/2004 |
| EP | 0 258 017 B2 | 12/2004 |
| EP | 1 482 944 A2 | 12/2004 |
| EP | 1 545 529 A2 | 6/2005 |
| EP | 1 144 385 B1 | 8/2005 |
| EP | 1 144 394 B1 | 8/2005 |
| EP | 1 575 943 A1 | 9/2005 |
| EP | 1 578 346 A2 | 9/2005 |
| EP | 1 578 736 A1 | 9/2005 |
| EP | 1 140 291 B1 | 11/2005 |
| EP | 1 144 371 B1 | 11/2005 |
| EP | 1 144 372 B1 | 11/2005 |
| EP | 1 673 339 A2 | 6/2006 |
| EP | 1 674 452 A1 | 6/2006 |
| EP | 1 682 138 A2 | 7/2006 |
| EP | 1 689 233 A2 | 8/2006 |
| EP | 0 993 437 B1 | 11/2006 |
| EP | 1 780 197 A1 | 5/2007 |
| EP | 1 799 656 A1 | 6/2007 |
| EP | 1 802 579 A1 | 7/2007 |
| EP | 1 838 675 A1 | 10/2007 |
| EP | 1 761 528 B1 | 1/2008 |
| EP | 1 894 932 A1 | 3/2008 |
| EP | 1 912 636 A2 | 4/2008 |
| EP | 1 922 307 A2 | 5/2008 |
| EP | 1 781 649 B1 | 8/2008 |
| EP | 1 966 155 A1 | 9/2008 |
| EP | 1 967 516 A1 | 9/2008 |
| EP | 1 791 837 B1 | 8/2009 |
| EP | 1 651 214 B1 | 9/2009 |
| EP | 1 828 184 B1 | 9/2009 |
| EP | 1 934 174 B1 | 4/2011 |
| ES | 2 229 515 T3 | 4/2005 |
| ES | 2 247 859 T3 | 3/2006 |
| ES | 2 249 060 T3 | 3/2006 |
| ES | 2 251 851 T3 | 5/2006 |
| ES | 2 252 996 T3 | 5/2006 |
| FR | 2 650 840 A1 | 2/1991 |
| GB | 2323845 | 10/1998 |
| JP | 2000-204075 A | 7/2000 |
| JP | 2000-204077 A | 7/2000 |
| JP | 2000-204079 A | 7/2000 |
| JP | 2000-212157 A | 8/2000 |
| JP | 2002-509536 A | 3/2002 |
| JP | 2002-511092 A | 4/2002 |
| JP | 2002-532570 A | 10/2002 |
| JP | 2002-534497 A | 10/2002 |
| JP | 2002-534510 A | 10/2002 |
| JP | 2002-534515 A | 10/2002 |
| JP | 2004-504294 A | 2/2004 |
| JP | 2005-508972 A | 4/2005 |
| JP | 2005-515251 A | 5/2005 |
| JP | 2005-515253 A | 5/2005 |
| JP | 2005-526008 A | 9/2005 |
| JP | 2005-526076 A | 9/2005 |
| JP | 2006-083133 A | 3/2006 |
| JP | 2006-508944 A | 3/2006 |
| JP | 2006-516967 A | 7/2006 |
| JP | 3811775 B2 | 8/2006 |
| JP | 2006-528621 A | 12/2006 |
| JP | 2007-504241 A | 3/2007 |
| JP | 2007-511614 A | 5/2007 |
| JP | 2007-511615 A | 5/2007 |
| JP | 2008-501631 A | 1/2008 |
| JP | 2008-509950 A | 4/2008 |
| JP | 2008-510839 A | 4/2008 |
| JP | 2008-513397 A | 5/2008 |
| JP | 2008-517024 A | 5/2008 |
| JP | 4090070 B2 | 5/2008 |
| JP | 2008-520615 A | 6/2008 |
| JP | 2008-521858 A | 6/2008 |
| JP | 4131741 B2 | 8/2008 |
| JP | 2008-201788 A | 9/2008 |
| KR | 10-2007-026343 | 3/2007 |
| KR | 10-2007-034581 | 3/2007 |
| KR | 10-2007-034635 | 3/2007 |
| KR | 10-2007-041752 | 4/2007 |
| KR | 10-2007-043895 | 4/2007 |
| KR | 10-2007-067727 | 6/2007 |
| KR | 10-2008-019236 | 3/2008 |
| KR | 10-2008-050601 | 6/2008 |
| KR | 10-2008-068637 | 7/2008 |
| RU | 2300528 C2 | 6/2007 |
| TR | 2001 01871 T2 | 10/2001 |
| TR | 2001 02029 T2 | 11/2001 |
| TR | 2001 02030 T2 | 1/2002 |
| TW | 396149 B | 7/2000 |
| TW | 592692 B | 6/2004 |
| WO | WO 91-02087 A1 | 2/1991 |
| WO | WO 92-15712 A1 | 9/1992 |
| WO | WO 94-09699 A1 | 5/1994 |
| WO | WO 95-06128 A2 | 3/1995 |
| WO | WO 99-01421 A1 | 1/1999 |
| WO | WO 99-01426 A1 | 1/1999 |
| WO | WO 00-37141 A1 | 6/2000 |
| WO | WO 00-41994 A1 | 7/2000 |
| WO | WO 00-42002 A1 | 7/2000 |
| WO | WO 00-42003 A1 | 7/2000 |
| WO | WO 00-42022 A1 | 7/2000 |
| WO | WO 00-42029 A1 | 7/2000 |
| WO | WO 02-06213 A2 | 1/2002 |
| WO | WO 03-035626 A2 | 5/2003 |
| WO | WO 03-047523 A2 | 6/2003 |
| WO | WO 03-047583 A1 | 6/2003 |
| WO | WO 03-047585 A1 | 6/2003 |
| WO | WO 03-062189 A1 | 7/2003 |
| WO | WO 03-062191 A1 | 7/2003 |
| WO | WO 03-077855 A2 | 9/2003 |
| WO | WO 2004-030620 A2 | 4/2004 |
| WO | WO 2004-041185 A2 | 5/2004 |
| WO | WO 2004-041811 A1 | 5/2004 |
| WO | WO 2004-044219 A2 | 5/2004 |
| WO | WO 2004-056789 A1 | 7/2004 |
| WO | WO 2005-000818 A1 | 1/2005 |
| WO | WO 2005-007616 A1 | 1/2005 |
| WO | WO 2005-009975 A2 | 2/2005 |
| WO | WO 2005-023759 A2 | 3/2005 |
| WO | WO 2005-028426 A1 | 3/2005 |
| WO | WO 2005-051301 A2 | 6/2005 |
| WO | WO 2005-051302 A2 | 6/2005 |
| WO | WO 2005-082891 A1 | 9/2005 |
| WO | WO 2005-121142 A1 | 12/2005 |
| WO | WO 2006-011466 A1 | 2/2006 |
| WO | WO 2006-018188 A2 | 2/2006 |

(56) References Cited

FOREIGN PATENT DOCUMENTS

| | | | |
|---|---|---|---|
| WO | WO 2006-024034 A1 | 3/2006 | |
| WO | WO 2006-029862 A1 | 3/2006 | |
| WO | WO 2006-045514 A1 | 5/2006 | |
| WO | WO 2006-056427 A1 | 6/2006 | |
| WO | WO 2006-058752 A1 | 6/2006 | |
| WO | WO 2006-133417 A1 | 12/2006 | |
| WO | WO 2007-014011 A2 | 2/2007 | |
| WO | WO 2007-025090 A2 | 3/2007 | |
| WO | WO 2007-044084 A2 | 4/2007 | |
| WO | WO 2007-044515 A1 | 4/2007 | |
| WO | WO 2007-071951 A1 | 6/2007 | |
| WO | WO 2007-096259 A1 | 8/2007 | |
| WO | WO 2007-121269 A2 | 10/2007 | |
| WO | WO 2007-121481 A2 | 10/2007 | |
| WO | WO 2007-123936 A1 | 11/2007 | |
| WO | WO 2007-123939 A2 | 11/2007 | |
| WO | WO 2008-021389 A2 | 2/2008 | |
| WO | WO 2008-024724 A1 | 2/2008 | |
| WO | WO 2008-024725 A1 | 2/2008 | |
| WO | WO 2008-055236 A2 | 5/2008 | |
| WO | WO 2008-067481 A1 | 6/2008 | |
| WO | WO 2008-076415 A1 | 6/2008 | |
| WO | WO2008079903 * | 7/2008 | ........... C07D 471/04 |
| ZA | 98-05726 | 6/1998 | |
| ZA | 98-05728 | 6/1998 | |
| ZA | 2001-005219 | 6/2001 | |
| ZA | 2001-005224 | 6/2001 | |

OTHER PUBLICATIONS

Velangi et al., BRAF gene is not mutated in mismatch repair-proficient or—deficient plasma cell dyscrasias, Leukemia, 18, 658-659, 2004.*

Bonello et al., BRAF gene is not mutated in plasma cell leukemia and multiple myeloma, Leukemia, 17, 2238-2240, 2003.*

Ng et al., Alterations of RAS signaling in Chinese multiple myeloma patients: absent BRAF and rare RAS mutations, but frequent inactivation of RASSF1A by transcriptional silencing or expression of a non-functional variant transcript, Brit. J. Haematology, 123, 637-645, 2003.*

Boobbyer, D. N. A. et al., "New Hydrogen-Bond Potentials for Use in Determining Energetically Favorable Binding Sites on Molecules of Known Structure," Journal of Medical Chemistry, vol. 32, No. 5, 1989, pp. 1083-1094.

Brünger A. T. et al, "Solution of a Protein Crystal Structure with a Model Obtained from NMR Interproton Distance Restraints," Science, vol. 235, 1987, pp. 1049-1053.

Brünger A. T. et al., "Crystallography & NMR System: A New Software Suite for Macromolecular Structure Determination," Acta Crystallography, vol. D54, 1998, pp. 905-921.

Carbonelli, D. L. et al., "A Plasmid Vector for Isolation of Strong Promoters in *Escherichia coli*," FEMS Microbiology Letters, vol. 177, 1999, pp. 75-82.

Carell, T. et al., "A Novel Procedure for the Synthesis of Libraries Containing Small Organic Molecules," Angewandte Chemie International Edition Engl., vol. 33, No. 20, 1994, pp. 2059-2061.

Carell T. et al., "A Solution-Phase Screening Procedure for the Isolation of Active Compounds from a Library of Molecules," Angewandte Chemie International Edition Engl., vol. 33, No. 20, 1994, pp. 2061-2064.

Chandler, S. D. et al., "RNA Splicing Specificity Determined by the Coordinated Action of RNA Recognition Motifs in SR Proteins," Proceedings of the National Academy of Sciences of the United States of America, vol. 94, 1997, pp. 3596-3601.

Chen, C. et al., "High-Efficiency Transformation of Mammalian Cells by Plasmid DNA," Molecular and Cellular Biology, vol. 7, No. 8, 1987, pp. 2745-2752.

Cocea, L. "Duplication of a Region in the Multiple Cloning Site of a Plasmid Vector to Enhance Cloning-Mediated Addition of Restriction Sites to a DNA Fragment," BioTechniques, vol. 23, No. 5, 1997, pp. 814-816.

Cull, M. G. et al., "Screening for receptor ligands using large libraries of peptides linked to the C terminus of the *lac* repressor," Proceedings of the National Academy of Sciences of the United States of America, vol. 89, 1992, pp. 1865-1869.

Cwirla, S. E. et al., "Peptides on Phage: A Vast Library of Peptides for Identifying Ligands," Proceedings of the National Academy of Sciences of the United States of America, vol. 87, 1990, pp. 6378-6382.

DesJarlias, R. L. et al., "Using Shape Complemenarity as an Initial Screen in Designing Lignads for a Receptor Binding Site of Known Three-Dimensional Structure," Journal of Medicinal Chemistry, vol. 31, No. 4, 1988, pp. 722-729.

Devlin, J. J. et al., "Random Peptide Libraries: A Source of Specific Protein Binding Molecules," Science, vol. 249, 1990, pp. 404-406.

Drenth, J., Ch. 1, "Crystallizing a Protein," Principles of Protein X-ray Crystallography, New York: Springer-Verlag, copyright 1994, pp. 1-19.

Erb, E. et al., "Recursive Deconvolution of Combinatorial Chemical Libraries," Proceedings of the National Academy of Sciences of the United States of America, vol. 91, 1994, pp. 11422-11426.

Fechheimer, M. et al., "Transfection of Mammalian Cells with Plasmid DNA by Scrape Loading and Sonication Loading," Proceedings of the National Academy of Sciences of the United States of America, vol. 84, 1987, pp. 8463-8467.

Felici, F. et al., "Selection of Antibody Ligands from a Large Library of Oligopeptides Expressed on a Multivalent Exposition Vector," Journal of Molecular Biology, vol. 222, 1991, pp. 301-310.

Fodor, S. P. A. et al., "Multiplexed Biochemical Assays with Biological Chips," Nature, vol. 364, 1993, pp. 555-556.

Fraley, R. T. et al., "Entrapment of a Bacterial Plasmid in Phospholipid Vesicles: Potential for Gene Transfer," Proceedings of the National Academy of Sciences of the United States of America, vol. 76, No. 7, 1979, pp. 3348-3352.

Froehler, B. C. et al., "Synthesis of DNA Via Deoxynucleoside H-phosphonate Intermediates," Nucleic Acids Research, vol. 14, No. 13, 1986, pp. 5399-5407.

Gallop, M. A. et al., "Applications of Combinatorial Technologies to Drug Discovery. 1. Background and Peptide Combinatorial Libraries," Journal of Medical Chemistry, vol. 37, No. 9, 1994, pp. 1233-1251.

Geromichalos, G. D., "Importance of Molecular Computer Modeling in Anitcancer Drug Development," Journal of Balkan Union of Oncology (BUON), vol. 12, Suppl. 1, 2007, pp. S101-S118.

Goodford, P. J. et al., "A Computational Procedure for Determining Energetically Favorable Binding Sites on Biologically Important Macromolecules," (1985) Journal of Medicinal Chemistry, vol. 28, pp. 849-857.

Gopal, T. V., "Gene Transfer Method for Transient Gene Expression, Stable Transformation, and Cotransformation of Suspension Cell Cultures," Molecular and Cellular Biology, vol. 5, No. 5, 1985, pp. 1188-1190.

Gossen, M. et al., "Tight control of gene expression in mammalian cells by tetracycline-responsive promoters," Proceedings of the National Academy of Sciences of the United States of America, vol. 89, 1992, pp. 5547-5551.

Gossen, M. et al., "Transcriptional Activation by Tetracyclines in Mammalian Cells," Science, vol. 268, 1995, pp. 1766-1769.

Graham, F. L. et al., "A New Technique for the Assay of Infectivity of Human Adenovirus 5 DNA," Virology, vol. 52, 1973, pp. 456-467.

Harland, R. et al., "Translation of mRNA Injected into Xenopus Oocytes Is Specifically Inhibited by Antisense RNA," Journal of Cell Biology, vol. 101, 1985, pp. 1094-1099.

Ho, C. M. W. et al., "Cavity Search: An Algorithm for the Isolation and Display of Cavity-Like Binding Regions," Journal of Computer-Aided Molecular Design, vol. 4, 1990, pp. 337-354.

Horwell, D. et al., "'Targeted' Molecular Diversity: Design and Development of Non-Peptide Antagonists for Cholecystokinin and Tachykinin Receptors," Immunopharmacology, vol. 33, 1996, pp. 68-72.

Houghten, R. A. et al., "The Use of Synthetic Peptide Combinatorial Libraries for the Identification of Bioactive Peptides," BioTechniques, vol. 13, No. 3, 1992, pp. 412-421.

International Search Report for International Application No. PCT/US2011/025645, dated May 9, 2011, 5 pages.

(56) References Cited

OTHER PUBLICATIONS

International Preliminary Report on Patentability for International Application No. PCT/US2011/025645, dated Aug. 28, 2012, 9 pages.
Kaeppler H. F. et al., "Silicon Carbide Fiber-Mediated DNA Delivery Into Plant Cells," Plant Cell Reports, vol. 9, 1990, pp. 415-418.
Kaneda, Y. et al., "Increased Expression of DNA Cointroduced with Nuclear Protein in Adult Rat Liver," Science, vol. 243, 1989, pp. 375-378.
Kato, K. et al., "Expression of Hepatitis B Virus Surface Antigen in Adult Rat Liver," Journal of Biological Chemistry, vol. 266, No. 6, 1991, pp. 3361-3364.
Kornher, J. S. et al., "Mutation Detection Using Nucleotide Analogs that Alter Electrophoretic Mobility," Nucleic Acids Research, vol. 17, No. 19, 1989, pp. 7779-7784.
Kuppuswamy, M. N. et al., "Single Nucleotide Primer Extension to Detect Genetic Diseases: Experimental Application to Hemophilia B (Factor IX) and Cystic Fibrosis Genes," Proceedings of the National Academy of Sciences of the United States of America, 1991, vol. 88, pp. 1143-1147.
Lam, K.S. et al., "A New Type of Synthetic Peptide Library for Identifying Ligand-Binding Activity," Nature, vol. 354, 1991, pp. 82-84.
Lam, K.S., Abstract of "Application of Combinatorial Library Methods in Cancer Research and Drug Discovery," Anticancer Drugs Design, vol. 12, No. 3, 1997, pp. 145-167.
Landegren et al., "A Ligase-Mediated Gene Detection Technique," Science, vol. 241, 1988, pp. 1077-1080.
Lawrence, Davis, "CLIX: A Search Algorithm for Finding Novel Ligands Capable of Binding Proteins of Known Three-Dimensional Structure," Proteins, Jan. 1992, vol. 12(1), pp. 31-41 (Abstract only), 1 page.
Levenson, V. V. et al., "Internal Ribosomal Entry Site-Containing Retroviral Vectors with Green Fluorescent Protein and Drug Resistance Markers," Human Gene Therapy, vol. 9, 1998, pp. 1233-1236.
Maxam, A. M., et al., "A New Method for Sequencing DNA," Proceedings of the National Academy of Sciences of the United States of America, vol. 74, No. 2, pp. 560-564, 1977.
Meng, E. C. et al., "Automated Docking with Grid-Based Energy Evaluation," Journal of Computational Chemistry, vol. 13, No. 4, 1992, pp. 505-524.
Meng, E. C. et al., "Orientational Sampling and Rigid-Body Minimization in Molecular Docking," Proteins: Structure, Function, and Genetics, vol. 17, 1993, pp. 266-278.
Mullis, K. et al., "Specific Enzymatic Amplification of DNA In Vitro: The Polymerase Chain Reaction," Cold Spring Harbor Symposia on Quantitative Biology, vol. 51, 1986, pp. 263-273.
Narula, S. S. et al., "Solution structure of the C-terminal SH2 domain of the human tyrosine kinase Syk complexed with a phosphotyrosine pentapeptide," Structure, vol. 3, No. 10, 1995, pp. 1061-1073.
Nickerson, D. A. et al., "Automated DNA Diagnostics Using an ELISA-based Oligonucleotide Ligation Assay," Proceedings of the National Academy of Sciences of the United States of America, vol. 87, 1990, pp. 8923-8927.
Nicolau, C. et al., "Liposome-Mediated DNA Transfer in Eukaryotic Cells. Dependence of the Transfer Efficiency Upon the Type of Liposomes Used and the Host Cell Cycle Stage," Biochimica et Biobhysica Acta, vol. 721, 1982, pp. 185-190.
Nicolau, C. et al., "Liposomes as Carriers for in Vivo Gene Transfer and Expression," Methods in Enzymology, vol. 149, 1987, pp. 157-176.
Nyrén, P. et al., "Solid Phase DNA Minisequencing by an Enzymatic Luminometric Inorganic Pryophosphate Detection Assay," Analytical Biochemistry, vol. 208, 1993, pp. 171-175.
Omirulleh, S. et al., "Activity of a Chimeric Promoter with the Doubled CaMV 35S Enhancer Element in Protoplast-Derived Cells and Transgenic Plains in Maize," Plant Molecular Biology, vol. 21, 1993, pp. 415-428.
Potrykus, I. et al., "Molecular and General Genetics of a Hybrid Foreign Gene Introduced into Tobacco by Direct Gene Transfer," Molecular and General Genetics, vol. 199, 1985, pp. 169-177.
Prezant, T. R. et al., "Trapped-Oligonucleotide Nucleotide Incorporation (TONI) Assay, a Simple Method for Screening Point Mutations," Human Mutation, vol. 1, 1992, pp. 159-164.
Rippe, R. A. et al., "DNA-Mediated Gene Transfer into Adult Rat Hepatocytes in Primary Culture," Molecular and Cellular Biology, vol. 10, No. 2, 1990, pp. 689-695.
Sanger, F., et al., Abstract of "A Rapid Method for Determining Sequences in DNA by Primed Synthesis with DNA Polymerase," Journal of Molecular Biology, vol. 94, No. 3, 1975, pp. 441-446.
Scott, J. K., et al., "Searching for Peptide Ligands with an Epitope Library," Science, 1990, vol. 249, pp. 386-390.
Shoichet, B. K. et al., "Structure-Based Discovery of Inhibitors of Thymidylate Synthase," Science, 1993, vol. 259, pp. 1445-1450.
Sokolov, B. P., "Primer Extension Technique for the Detection of Single Nucleotide in Genomic DNA," Nucleic Acids Research, vol. 18, No. 12, 1989, pp. 3671.
Stevens, R. C. et al., "High-throughput protein crystallization," Current Opinion in Structural Biology, vol. 10, 2000, pp. 558-563.
Syvänen, A.-C. et al., "Identification of Individuals by Analysis of Biallelic DNA Markers, Using PCR and Solid-Phase Minisequencing," American Journal of Human Genetics, vol. 52, 1993, pp. 46-59.
Ugozzolli, L. et al., "Detection of Specific Alleles by Using Allele-Specific Primer Extension Followed by Capture on Solid Support," Genetic Analysis, Techniques and Applications, vol. 9, No. 4, 1992, pp. 107-112.
Wong, T-K. et al., "Appearance of β-lactamase activity in animal cells upon liposome-mediated gene transfer," Gene, vol. 10, 1980, pp. 87-94.

* cited by examiner

Figure 1: Homo sapiens BRAF nucleic acid sequence (SEQ ID NO:1)
(NCBI Reference Sequence: NM_004333.4; gi 187608632)

```
CGCCTCCCTTCCCCCTCCCCGCCCGACAGCGGCCGCTCGGGCCCCGGCTCTCGGTTATAAGAT
GGCGGCGCTGAGCGGTGGCGGTGGTGGCGGCGCGGAGCCGGGCCAGGCTCTGTTCAACGGG
GACATGGAGCCCGAGGCCGGCGCCGGCGCCGGCGCCGCGGCCTCTTCGGCTGCGGACCCTG
CCATTCCGGAGGAGGTGTGGAATATCAAACAAATGATTAAGTTGACACAGGAACATATAGAGGC
CCTATTGGACAAATTTGGTGGGGAGCATAATCCACCATCAATATATCTGGAGGCCTATGAAGAAT
ACACCAGCAAGCTAGATGCACTCCAACAAAGAGAACAACAGTTATTGGAATCTCTGGGGAACGG
AACTGATTTTTCTGTTTCTAGCTCTGCATCAATGGATACCGTTACATCTTCTTCCTCTTCTAGCCT
TTCAGTGCTACCTTCATCTCTTTCAGTTTTTCAAAATCCCACAGATGTGGCACGGAGCAACCCCA
AGTCACCACAAAAACCTATCGTTAGAGTCTTCCTGCCCAACAAACAGAGGACAGTGGTACCTGC
AAGGTGTGGAGTTACAGTCCGAGACAGTCTAAAGAAAGCACTGATGATGAGAGGTCTAATCCCA
GAGTGCTGTGCTGTTTACAGAATTCAGGATGGAGAGAAGAAACCAATTGGTTGGGACACTGATA
TTTCCTGGCTTACTGGAGAAGAATTGCATGTGGAAGTGTTGGAGAATGTTCCACTTACAACACAC
AACTTTGTACGAAAAACGTTTTTCACCTTAGCATTTTGTGACTTTTGTCGAAAGCTGCTTTTCCAG
GGTTTCCGCTGTCAAACATGTGGTTATAAATTTCACCAGCGTTGTAGTACAGAAGTTCCACTGAT
GTGTGTTAATTATGACCAACTTGATTTGCTGTTTGTCTCCAAGTTCTTTGAACACCACCCAATACC
ACAGGAAGAGGCGTCCTTAGCAGAGACTGCCCTAACATCTGGATCATCCCCTTCCGCACCCGC
CTCGGACTCTATTGGGCCCCAAATTCTCACCAGTCCGTCTCCTTCAAAATCCATTCCAATTCCAC
AGCCCTTCCGACCAGCAGATGAAGATCATCGAAATCAATTTGGGCAACGAGACCGATCCTCATC
AGCTCCCAATGTGCATATAAACACAATAGAACCTGTCAATATTGATGACTTGATTAGAGACCAAG
GATTTCGTGGTGATGGAGGATCAACCACAGGTTTGTCTGCTACCCCCCCTGCCTCATTACCTGG
CTCACTAACTAACGTGAAAGCCTTACAGAAATCTCCAGGACCTCAGCGAGAAAGGAAGTCATCTT
CATCCTCAGAAGACAGGAATCGAATGAAAACACTTGGTAGACGGGACTCGAGTGATGATTGGGA
GATTCCTGATGGGCAGATTACAGTGGGACAAAGAATTGGATCTGGATCATTTGGAACAGTCTACA
AGGGAAAGTGGCATGGTGATGTGGCAGTGAAAATGTTGAATGTGACAGCACCTACACCTCAGCA
GTTACAAGCCTTCAAAAATGAAGTAGGAGTACTCAGGAAAACACGACATGTGAATATCCTACTCT
TCATGGGCTATTCCACAAAGCCACAACTGGCTATTGTTACCCAGTGGTGTGAGGGCTCCAGCTT
GTATCACCATCTCCATATCATTGAGACCAAATTTGAGATGATCAAACTTATAGATATTGCACGACA
GACTGCACAGGGCATGGATTACTTACACGCCAAGTCAATCATCCACAGAGACCTCAAGAGTAAT
AATATATTTCTTCATGAAGACCTCACAGTAAAAATAGGTGATTTTGGTCTAGCTACAGTGAAATCT
CGATGGAGTGGGTCCCATCAGTTTGAACAGTTGTCTGGATCCATTTTGTGGATGGCACCAGAAG
TCATCAGAATGCAAGATAAAAATCCATACAGCTTTCAGTCAGATGTATATGCATTTGGAATTGTTC
TGTATGAATTGATGACTGGACAGTTACCTTATTCAAACATCAACAACAGGGACCAGATAATTTTTA
TGGTGGGACGAGGATACCTGTCTCCAGATCTCAGTAAGGTACGGAGTAACTGTCCAAAAGCCAT
GAAGAGATTAATGGCAGAGTGCCTCAAAAAGAAAAGAGATGAGAGACCACTCTTTCCCCAAATTC
TCGCCTCTATTGAGCTGCTGGCCCGCTCATTGCCAAAAATTCACCGCAGTGCATCAGAACCCTC
CTTGAATCGGGCTGGTTTCCAAACAGAGGATTTTAGTCTATATGCTTGTGCTTCTCCAAAAACAC
CCATCCAGGCAGGGGGATATGGTGCGTTTCCTGTCCACTGAAACAAATGAGTGAGAGAGTTCAG
GAGAGTAGCAACAAAAGGAAAATAAATGAACATATGTTTGCTTATATGTTAAATTGAATAAAATAC
TCTCTTTTTTTTTAAGGTGAACCAAAGAACACTTGTGTGGTTAAAGACTAGATATAATTTTTCCCC
AAACTAAAATTTATACTTAACATTGGATTTTTAACATCCAAGGGTTAAAATACATAGACATTGCTAA
AAATTGGCAGAGCCTCTTCTAGAGGCTTTACTTTCTGTTCCGGGTTTGTATCATTCACTTGGTTAT
TTTAAGTAGTAAACTTCAGTTTCTCATGCAACTTTTGTTGCCAGCTATCACATGTCCACTAGGGAC
TCCAGAAGAAGACCCTACCTATGCCTGTGTTTGCAGGTGAGAAGTTGGCAGTCGGTTAGCCTGG
GTTAGATAAGGCAAACTGAACAGATCTAATTTAGGAAGTCAGTAGAATTTAATAATTCTATTATTAT
TCTTAATAATTTTTCTATAACTATTTCTTTTTATAACAATTTGGAAAATGTGGATGTCTTTTATTTCC
TTGAAGCAATAAACTAAGTTTCTTTTTATAAAAA
```

Figure 2: Homo sapiens BRAF polypeptide sequence (SEQ ID NO:2)
(NCBI Reference Sequence: NP_004324.2; gi 33188459 )

```
MAALSGGGGGGAEPGQALFNGDMEPEAGAGAGAAASSAADPAIPEEVWNIKQMIKLTQEHIEALL
DKFGGEHNPPSIYLEAYEEYTSKLDALQQREQQLLESLGNGTDFSVSSSASMDTVTSSSSSSLSV
LPSSLSVFQNPTDVARSNPKSPQKPIVRVFLPNKQRTVVPARCGVTVRDSLKKALMMRGLIPECC
AVYRIQDGEKKPIGWDTDISWLTGEELHVEVLENVPLTTHNFVRKTFFTLAFCDFCRKLLFQGFRC
QTCGYKFHQRCSTEVPLMCVNYDQLDLLFVSKFFEHHPIPQEEASLAETALTSGSSPSAPASDSIG
PQILTSPSPSKSIPIPQPFRPADEDHRNQFGQRDRSSSAPNVHINTIEPVNIDDLIRDQGFRGDGGS
TTGLSATPPASLPGSLTNVKALQKSPGPQRERKSSSSSEDRNRMKTLGRRDSSDDWEIPDGQITV
GQRIGSGSFGTVYKGKWHGDVAVKMLNVTAPTPQQLQAFKNEVGVLRKTRHVNILLFMGYSTKP
QLAIVTQWCEGSSLYHHLHIIETKFEMIKLIDIARQTAQGMDYLHAKSIIHRDLKSNNIFLHEDLTVKIG
DFGLATVKSRWSGSHQFEQLSGSILWMAPEVIRMQDKNPYSFQSDVYAFGIVLYELMTGQLPYSN
INNRDQIIFMVGRGYLSPDLSKVRSNCPKAMKRLMAECLKKKRDERPLFPQILASIELLARSLPKIHR
SASEPSLNRAGFQTEDFSLYACASPKTPIQAGGYGAFPVH
```

Figure 3: Homo sapiens BRAF V600E nucleic acid sequence (SEQ ID NO:3)

```
CGCCTCCCTTCCCCCTCCCCGCCCGACAGCGGCCGCTCGGGCCCCGGCTCTCGGTTATAAGAT
GGCGGCGCTGAGCGGTGGCGGTGGTGGCGGCGCGGAGCCGGGCCAGGCTCTGTTCAACGGG
GACATGGAGCCCGAGGCCGGCGCCGGCGCCGGCGCCGCGGCCTCTTCGGCTGCGGACCCTG
CCATTCCGGAGGAGGTGTGGAATATCAAACAAATGATTAAGTTGACACAGGAACATATAGAGGC
CCTATTGGACAAATTTGGTGGGGAGCATAATCCACCATCAATATATCTGGAGGCCTATGAAGAAT
ACACCAGCAAGCTAGATGCACTCCAACAAAGAGAACAACAGTTATTGGAATCTCTGGGGAACGG
AACTGATTTTTCTGTTTCTAGCTCTGCATCAATGGATACCGTTACATCTTCTTCCTCTTCTAGCCT
TTCAGTGCTACCTTCATCTCTTTCAGTTTTTCAAAATCCCACAGATGTGGCACGGAGCAACCCCA
AGTCACCACAAAAACCTATCGTTAGAGTCTTCCTGCCCAACAAACAGAGGACAGTGGTACCTGC
AAGGTGTGGAGTTACAGTCCGAGACAGTCTAAAGAAAGCACTGATGATGAGAGGTCTAATCCCA
GAGTGCTGTGCTGTTTACAGAATTCAGGATGGAGAGAAGAAACCAATTGGTTGGGACACTGATA
TTTCCTGGCTTACTGGAGAAGAATTGCATGTGGAAGTGTTGGAGAATGTTCCACTTACAACACAC
AACTTTGTACGAAAAACGTTTTTCACCTTAGCATTTTGTGACTTTTGTCGAAAGCTGCTTTTCCAG
GGTTTCCGCTGTCAAACATGTGGTTATAAATTTCACCAGCGTTGTAGTACAGAAGTTCCACTGAT
GTGTGTTAATTATGACCAACTTGATTTGCTGTTTGTCTCCAAGTTCTTTGAACACCACCCAATACC
ACAGGAAGAGGCGTCCTTAGCAGAGACTGCCCTAACATCTGGATCATCCCCTTCCGCACCCGC
CTCGGACTCTATTGGGCCCCAAATTCTCACCAGTCCGTCTCCTTCAAAATCCATTCCAATTCCAC
AGCCCTTCCGACCAGCAGATGAAGATCATCGAAATCAATTTGGGCAACGAGACCGATCCTCATC
AGCTCCCAATGTGCATATAAACACAATAGAACCTGTCAATATTGATGACTTGATTAGAGACCAAG
GATTTCGTGGTGATGGAGGATCAACCACAGGTTTGTCTGCTACCCCCCCTGCCTCATTACCTGG
CTCACTAACTAACGTGAAAGCCTTACAGAAATCTCCAGGACCTCAGCGAGAAAGGAAGTCATCTT
CATCCTCAGAAGACAGGAATCGAATGAAAACACTTGGTAGACGGGACTCGAGTGATGATTGGGA
GATTCCTGATGGGCAGATTACAGTGGGACAAAGAATTGGATCTGGATCATTTGGAACAGTCTACA
AGGGAAAGTGGCATGGTGATGTGGCAGTGAAAATGTTGAATGTGACAGCACCTACACCTCAGCA
GTTACAAGCCTTCAAAAATGAAGTAGGAGTACTCAGGAAAACACGACATGTGAATATCCTACTCT
TCATGGGCTATTCCACAAAGCCACAACTGGCTATTGTTACCCAGTGGTGTGAGGGCTCCAGCTT
GTATCACCATCTCCATATCATTGAGACCAAATTTGAGATGATCAAACTTATAGATATTGCACGACA
GACTGCACAGGGCATGGATTACTTACACGCCAAGTCAATCATCCACAGAGACCTCAAGAGTAAT
AATATATTTCTTCATGAAGACCTCACAGTAAAAATAGGTGATTTTGGTCTAGCTACAGAGAAATCT
CGATGGAGTGGGTCCCATCAGTTTGAACAGTTGTCTGGATCCATTTTGTGGATGGCACCAGAAG
TCATCAGAATGCAAGATAAAAATCCATACAGCTTTCAGTCAGATGTATATGCATTTGGAATTGTTC
TGTATGAATTGATGACTGGACAGTTACCTTATTCAAACATCAACAACAGGGACCAGATAATTTTTA
TGGTGGGACGAGGATACCTGTCTCCAGATCTCAGTAAGGTACGGAGTAACTGTCCAAAAGCCAT
GAAGAGATTAATGGCAGAGTGCCTCAAAAAGAAAAGAGATGAGAGACCACTCTTTCCCCAAATTC
TCGCCTCTATTGAGCTGCTGGCCCGCTCATTGCCAAAAATTCACCGCAGTGCATCAGAACCCTC
CTTGAATCGGGCTGGTTTCCAAACAGAGGATTTTAGTCTATATGCTTGTGCTTCTCCAAAAACAC
CCATCCAGGCAGGGGGATATGGTGCGTTTCCTGTCCACTGAAACAAATGAGTGAGAGAGTTCAG
GAGAGTAGCAACAAAAGGAAAATAAATGAACATATGTTTGCTTATATGTTAAATTGAATAAAATAC
TCTCTTTTTTTTTAAGGTGAACCAAAGAACACTTGTGTGGTTAAAGACTAGATATAATTTTTTCCCC
AAACTAAAATTTATACTTAACATTGGATTTTTAACATCCAAGGGTTAAAATACATAGACATTGCTAA
AAATTGGCAGAGCCTCTTCTAGAGGCTTTACTTTCTGTTCCGGGTTTGTATCATTCACTTGGTTAT
TTTAAGTAGTAAACTTCAGTTTCTCATGCAACTTTTGTTGCCAGCTATCACATGTCCACTAGGGAC
TCCAGAAGAAGACCCTACCTATGCCTGTGTTTGCAGGTGAGAAGTTGGCAGTCGGTTAGCCTGG
GTTAGATAAGGCAAACTGAACAGATCTAATTTAGGAAGTCAGTAGAATTTAATAATTCTATTATTAT
TCTTAATAATTTTTCTATAACTATTTCTTTTTATAACAATTTGGAAAATGTGGATGTCTTTTATTTCC
TTGAAGCAATAAACTAAGTTTCTTTTTATAAAAA
```

Figure 4: Homo sapiens BRAF V600E polypeptide sequence (SEQ ID NO:4)

MAALSGGGGGGAEPGQALFNGDMEPEAGAGAGAAASSAADPAIPEEVWNIKQMIKLTQEHIEALL
DKFGGEHNPPSIYLEAYEEYTSKLDALQQREQQLLESLGNGTDFSVSSSASMDTVTSSSSSSLSV
LPSSLSVFQNPTDVARSNPKSPQKPIVRVFLPNKQRTVVPARCGVTVRDSLKKALMMRGLIPECC
AVYRIQDGEKKPIGWDTDISWLTGEELHVEVLENVPLTTHNFVRKTFFTLAFCDFCRKLLFQGFRC
QTCGYKFHQRCSTEVPLMCVNYDQLDLLFVSKFFEHHPIPQEEASLAETALTSGSSPSAPASDSIG
PQILTSPSPSKSIPIPQPFRPADEDHRNQFGQRDRSSSAPNVHINTIEPVNIDDLIRDQGFRGDGGS
TTGLSATPPASLPGSLTNVKALQKSPGPQRERKSSSSSEDRNRMKTLGRRDSSDDWEIPDGQITV
GQRIGSGSFGTVYKGKWHGDVAVKMLNVTAPTPQQLQAFKNEVGVLRKTRHVNILLFMGYSTKP
QLAIVTQWCEGSSLYHHLHIIETKFEMIKLIDIARQTAQGMDYLHAKSIIHRDLKSNNIFLHEDLTVKIG
DFGLATEKSRWSGSHQFEQLSGSILWMAPEVIRMQDKNPYSFQSDVYAFGIVLYELMTGQLPYSN
INNRDQIIFMVGRGYLSPDLSKVRSNCPKAMKRLMAECLKKKRDERPLFPQILASIELLARSLPKIHR
SASEPSLNRAGFQTEDFSLYACASPKTPIQAGGYGAFPVH

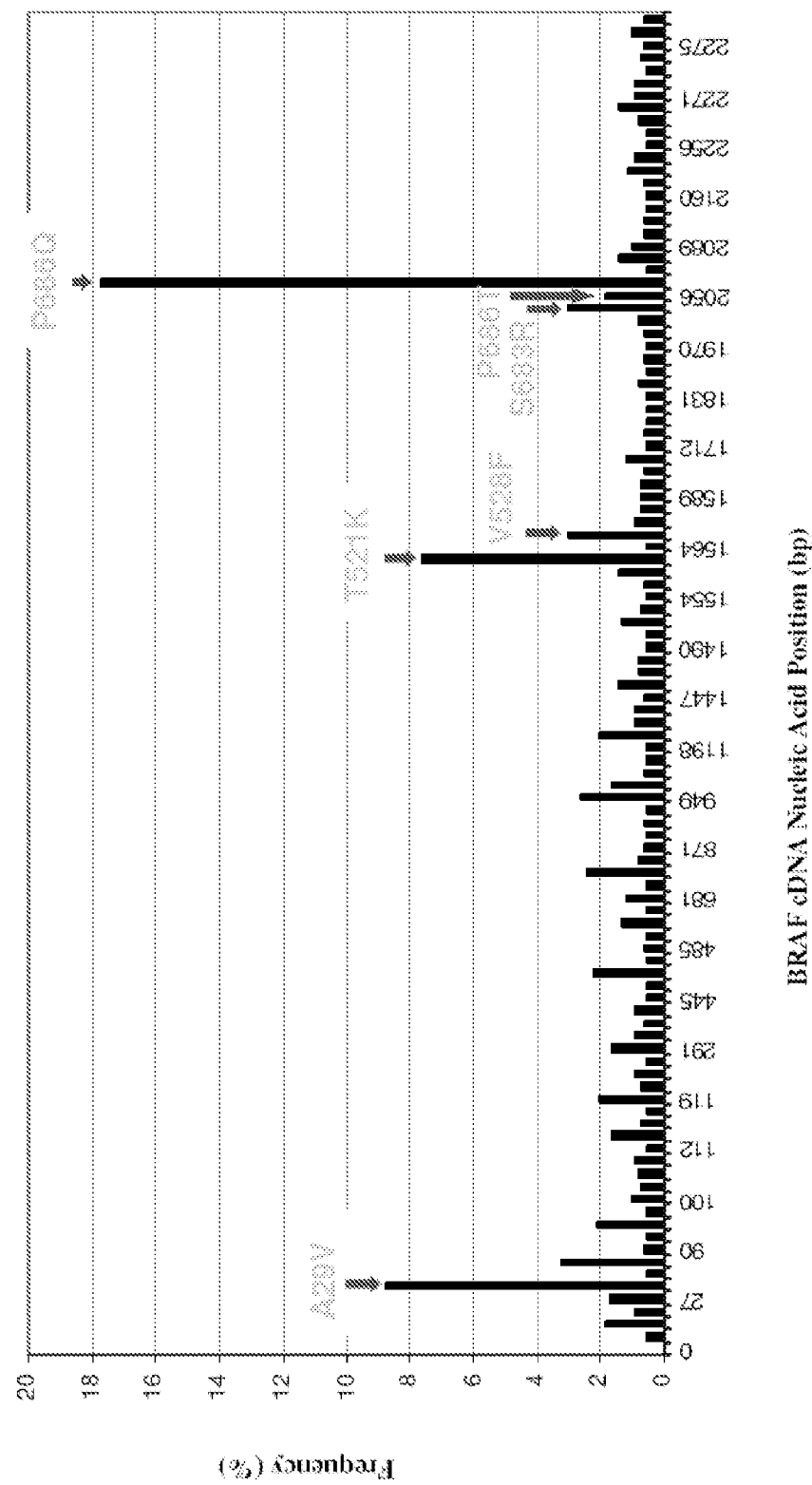
Figure 5: BRAF Mutational Landscape Following RAF265 Selection

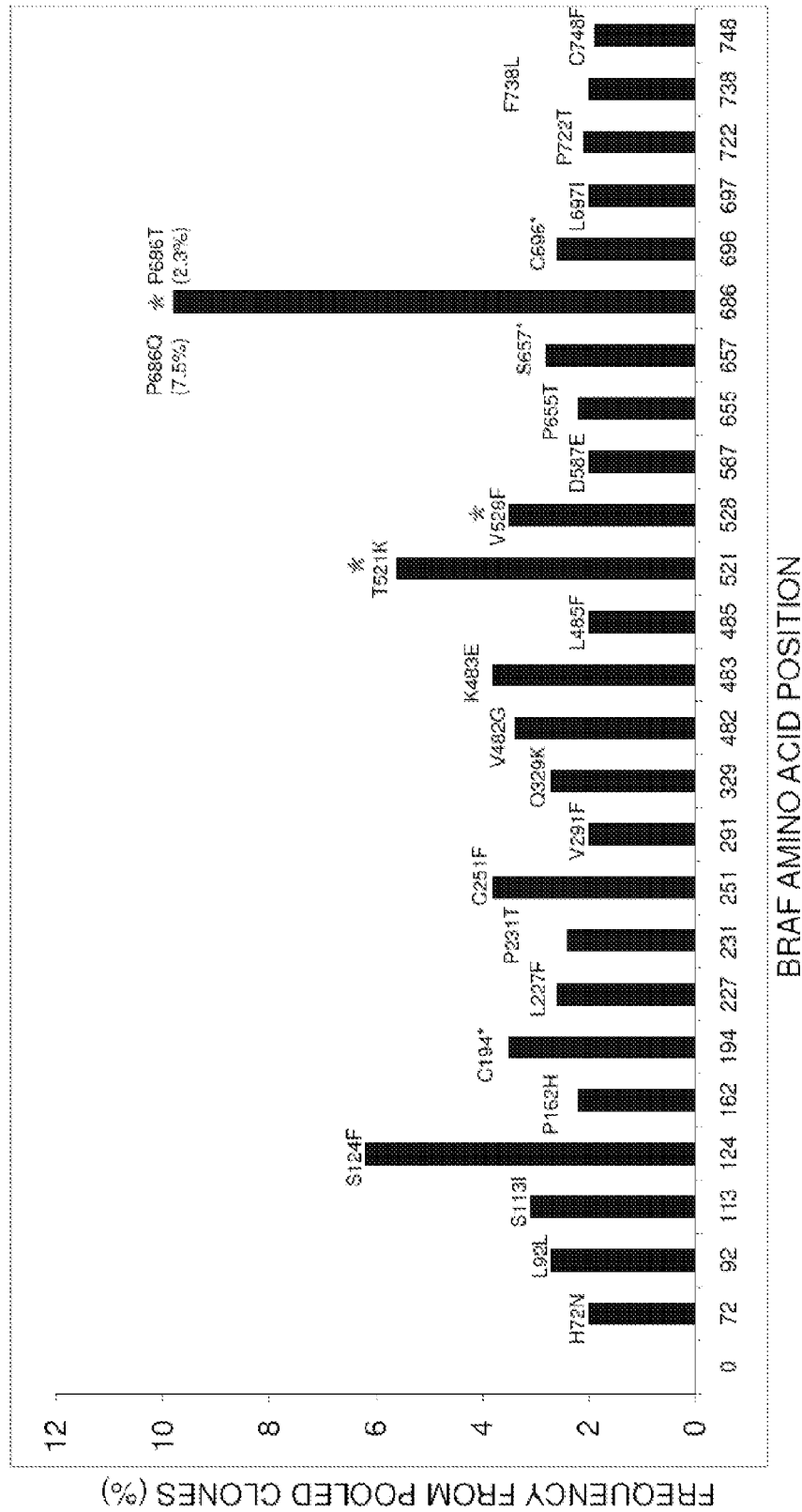
Figure 6: BRAF Mutational Landscape Following PLX4720 Selection

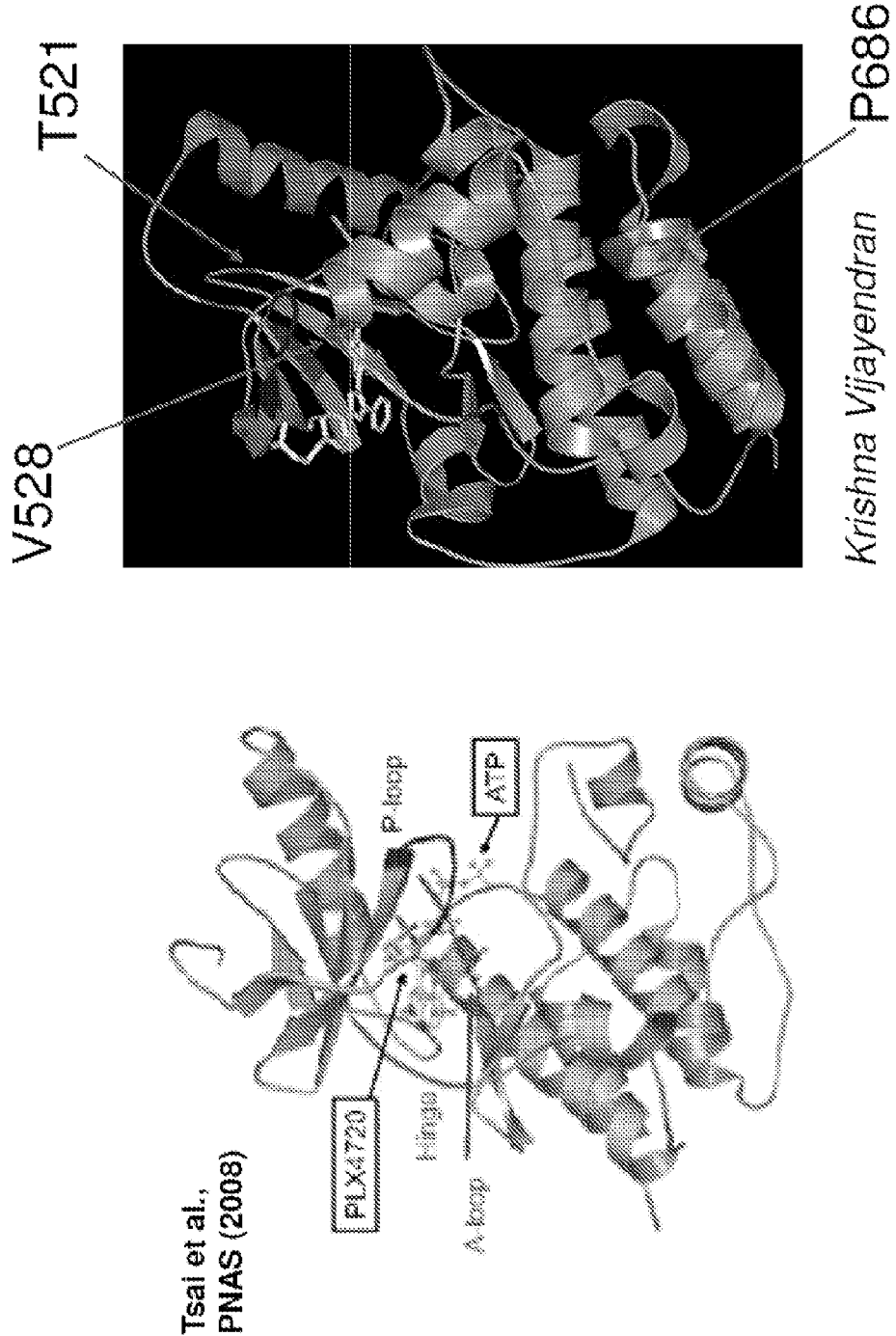
Figure 7: BRAF Mutations Common to Both RAF265 and PLX4720 Screen

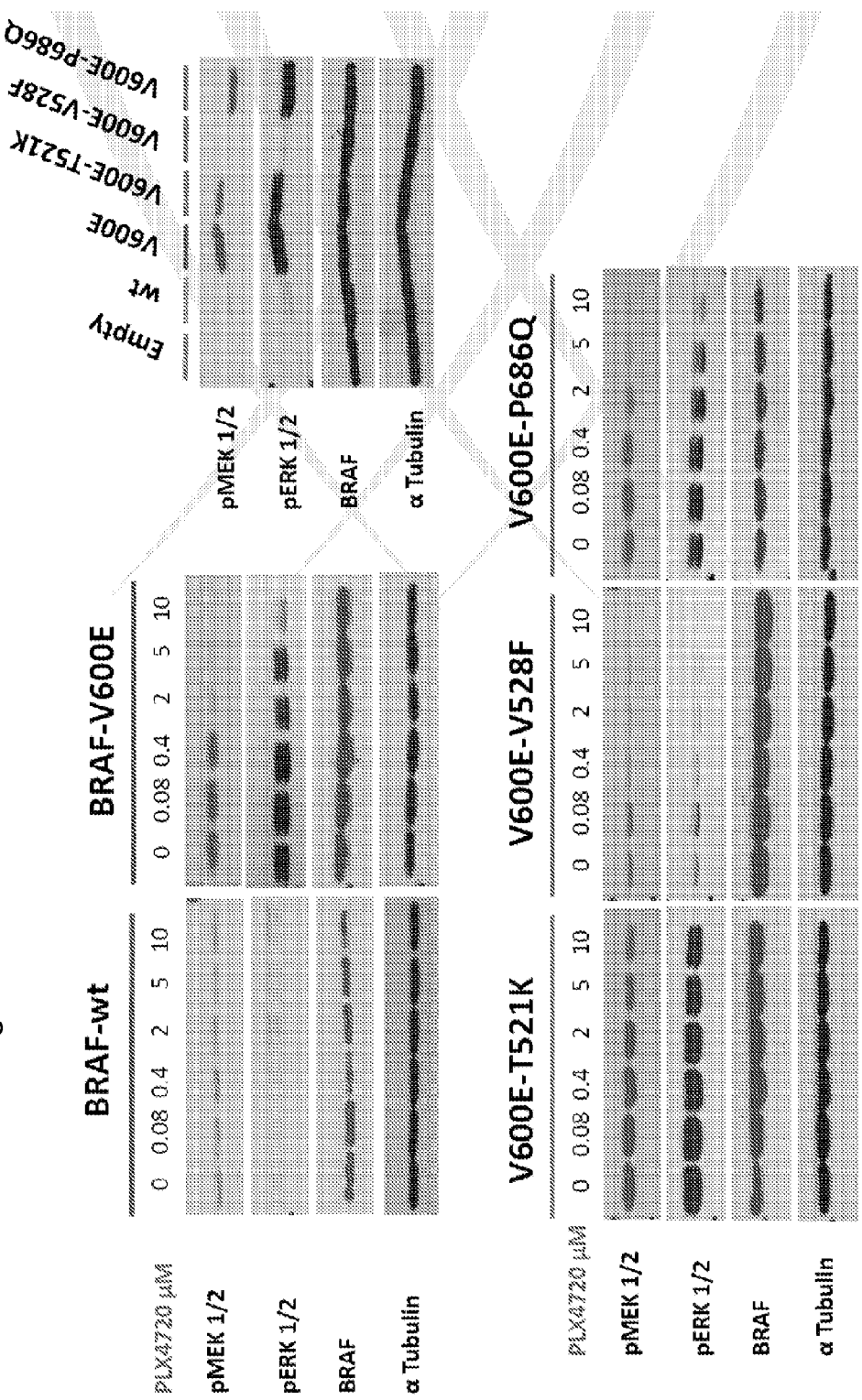
Figure 8: Immunoblot studies of BRAF, p-MEK1/2 and p-ERK1/2 levels following treatment with increasing concentrations of PLX4720

SEQUENCE LISTING

<160> NUMBER OF SEQ ID NOS: 4

<210> SEQ ID NO 1
<211> LENGTH: 2949
<212> TYPE: DNA
<213> ORGANISM: Homo sapiens

<400> SEQUENCE: 1

| | | | | | | |
|---|---|---|---|---|---|---|
| cgcctcccttt | cccctcccc | gcccgacagc | ggccgctcgg | gccccggctc | tcggttataa | 60 |
| gatggcggcg | ctgagcggtg | gcggtggtgg | cggcgcggag | ccgggccagg | ctctgttcaa | 120 |
| cggggacatg | gagcccgagg | ccggcgccgg | cgccggcgcc | gcggcctctt | cggctgcgga | 180 |
| ccctgccatt | ccgaggagg | tgtggaatat | caaacaaatg | attaagttga | cacaggaaca | 240 |
| tatagaggcc | ctattggaca | aatttggtgg | ggagcataat | ccaccatcaa | tatatctgga | 300 |
| ggcctatgaa | gaatacacca | gcaagctaga | tgcactccaa | caaagagaac | aacagttatt | 360 |
| ggaatctctg | gggaacggaa | ctgatttttc | tgtttctagc | tctgcatcaa | tggataccgt | 420 |
| tacatcttct | tcctcttcta | gcctttcagt | gctaccttca | tctctttcag | tttttcaaaa | 480 |
| tcccacagat | gtggcacgga | gcaaccccaa | gtcaccacaa | aaacctatcg | ttagagtctt | 540 |
| cctgcccaac | aaacagagga | cagtggtacc | tgcaaggtgt | ggagttacag | tccgagacag | 600 |
| tctaaagaaa | gcactgatga | tgagaggtct | aatcccagag | tgctgtgctg | tttacagaat | 660 |
| tcaggatgga | gagaagaaac | caattggttg | ggacactgat | atttcctggc | ttactggaga | 720 |
| agaattgcat | gtggaagtgt | tggagaatgt | tccacttaca | acacacaact | ttgtacgaaa | 780 |
| aacgtttttc | accttagcat | tttgtgactt | ttgtcgaaag | ctgcttttcc | agggtttccg | 840 |
| ctgtcaaaca | tgtggttata | aatttcacca | gcgttgtagt | acagaagttc | cactgatgtg | 900 |
| tgttaattat | gaccaacttg | atttgctgtt | tgtctccaag | ttctttgaac | caccccaat | 960 |
| accacaggaa | gaggcgtcct | tagcagagac | tgccctaaca | tctggatcat | cccttccgc | 1020 |
| acccgcctcg | gactctattg | ggccccaaat | tctcaccagt | ccgtctcctt | caaaatccat | 1080 |
| tccaattcca | cagcccttcc | gaccagcaga | tgaagatcat | cgaaatcaat | ttgggcaacg | 1140 |
| agaccgatcc | tcatcagctc | ccaatgtgca | tataaacaca | atagaacctg | tcaatattga | 1200 |
| tgacttgatt | agagaccaag | gatttcgtgg | tgatggagga | tcaaccacag | gtttgtctgc | 1260 |
| tacccccct | gcctcattac | ctggctcact | aactaacgtg | aaagccttac | agaaatctcc | 1320 |
| aggacctcag | cgagaaagga | agtcatcttc | atcctcagaa | gacaggaatc | gaatgaaaac | 1380 |
| acttggtaga | cgggactcga | gtgatgattg | ggagattcct | gatgggcaga | ttacagtggg | 1440 |
| acaaagaatt | ggatctggat | catttggaac | agtctacaag | ggaaagtggc | atggtgatgt | 1500 |
| ggcagtgaaa | atgttgaatg | tgacagcacc | tacacctcag | cagttacaag | ccttcaaaaa | 1560 |
| tgaagtagga | gtactcagga | aaacacgaca | tgtgaatatc | ctactcttca | tgggctatc | 1620 |
| cacaaagcca | caactggcta | ttgttaccca | gtggtgtgag | ggctccagct | tgtatcacca | 1680 |
| tctccatatc | attgagacca | aatttgagat | gatcaaactt | atagatattg | cacgacagac | 1740 |
| tgcacagggc | atggattact | tacacgccaa | gtcaatcatc | cacagagacc | tcaagagtaa | 1800 |
| taatatattt | cttcatgaag | acctcacagt | aaaaataggt | gattttggtc | tagctacagt | 1860 |
| gaaatctcga | tggagtgggt | cccatcagtt | tgaacagttg | tctggatcca | ttttgtggat | 1920 |
| ggcaccagaa | gtcatcagaa | tgcaagataa | aaatccatac | agctttcagt | cagatgtata | 1980 |
| tgcatttgga | attgttctgt | atgaattgat | gactggacag | ttaccttatt | caaacatcaa | 2040 |

```
caacagggac cagataattt ttatggtggg acgaggatac ctgtctccag atctcagtaa    2100
ggtacggagt aactgtccaa aagccatgaa gagattaatg gcagagtgcc tcaaaaagaa    2160
aagagatgag agaccactct ttccccaaat tctcgcctct attgagctgc tggcccgctc    2220
attgccaaaa attcaccgca gtgcatcaga accctccttg aatcgggctg gtttccaaac    2280
agaggatttt agtctatatg cttgtgcttc tccaaaaaca cccatccagg caggggata     2340 tggtgcgttt cctgtccact gaaacaaatg agtgagagag ttcaggagag tagcaacaaa    2400
aggaaaataa atgaacatat gtttgcttat atgttaaatt gaataaaata ctctcttttt    2460
ttttaaggtg aaccaaagaa cacttgtgtg gttaaagact agatataatt tttcccccaaa   2520 ctaaaattta tacttaacat tggatttta acatccaagg gttaaaatac atagacattg     2580
ctaaaaattg gcagagcctc ttctagaggc tttactttct gttccgggtt tgtatcattc    2640
acttggttat tttaagtagt aaacttcagt ttctcatgca acttttgttg ccagctatca    2700
catgtccact agggactcca gaagaagacc ctacctatgc ctgtgtttgc aggtgagaag    2760
ttggcagtcg gttagcctgg gttagataag gcaaactgaa cagatctaat ttaggaagtc    2820
agtagaattt aataattcta ttattattct taataatttt tctataacta tttcttttta    2880
taacaatttg gaaaatgtgg atgtctttta tttccttgaa gcaataaact aagtttcttt    2940
ttataaaaa                                                            2949

<210> SEQ ID NO 2
<211> LENGTH: 766
<212> TYPE: PRT
<213> ORGANISM: Homo sapiens

<400> SEQUENCE: 2

Met Ala Ala Leu Ser Gly Gly Gly Gly Gly Ala Glu Pro Gly Gln
1               5                  10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
```

```
              210                 215                 220
Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
                260                 265                 270

Ser Thr Glu Val Pro Leu Met Cys Val Asn Tyr Asp Gln Leu Asp Leu
            275                 280                 285

Leu Phe Val Ser Lys Phe Phe Glu His His Pro Ile Pro Gln Glu Glu
        290                 295                 300

Ala Ser Leu Ala Glu Thr Ala Leu Thr Ser Gly Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
                340                 345                 350

His Arg Asn Gln Phe Gly Gln Arg Asp Arg Ser Ser Ala Pro Asn
            355                 360                 365

Val His Ile Asn Thr Ile Glu Pro Val Asn Ile Asp Leu Ile Arg
        370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser
            420                 425                 430

Glu Asp Arg Asn Arg Met Lys Thr Leu Gly Arg Arg Asp Ser Ser Asp
            435                 440                 445

Asp Trp Glu Ile Pro Asp Gly Gln Ile Thr Val Gly Gln Arg Ile Gly
        450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
            500                 505                 510

Ile Leu Leu Phe Met Gly Tyr Ser Thr Lys Pro Gln Leu Ala Ile Val
        515                 520                 525

Thr Gln Trp Cys Glu Gly Ser Ser Leu Tyr His His Leu His Ile Ile
    530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
            580                 585                 590

Gly Asp Phe Gly Leu Ala Thr Val Lys Ser Arg Trp Ser Gly Ser His
        595                 600                 605

Gln Phe Glu Gln Leu Ser Gly Ser Ile Leu Trp Met Ala Pro Glu Val
    610                 615                 620

Ile Arg Met Gln Asp Lys Asn Pro Tyr Ser Phe Gln Ser Asp Val Tyr
625                 630                 635                 640
```

```
Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
            660                 665                 670

Tyr Leu Ser Pro Asp Leu Ser Lys Val Arg Ser Asn Cys Pro Lys Ala
        675                 680                 685

Met Lys Arg Leu Met Ala Glu Cys Leu Lys Lys Lys Arg Asp Glu Arg
    690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
            740                 745                 750

Thr Pro Ile Gln Ala Gly Gly Tyr Gly Ala Phe Pro Val His
        755                 760                 765

<210> SEQ ID NO 3
<211> LENGTH: 2949
<212> TYPE: DNA
<213> ORGANISM: Homo sapiens

<400> SEQUENCE: 3
cgcctccctt ccccctcccc gcccgacagc ggccgctcgg gccccggctc tcggttataa      60
gatggcggcg ctgagcggtg gcggtggtgg cggcgcggag ccgggccagg ctctgttcaa     120
cggggacatg gagcccgagg ccggcgccgg cgccggcgcc gcggcctctt cggctgcgga     180
ccctgccatt ccgaggagg tgtggaatat caaacaaatg attaagttga cacaggaaca      240
tatagaggcc ctattggaca aatttggtgg ggagcataat ccaccatcaa tatatctgga     300
ggcctatgaa gaatacacca gcaagctaga tgcactccaa caaagagaac aacagttatt     360
ggaatctctg gggaacggaa ctgattttc tgtttctagc tctgcatcaa tggataccgt      420
tacatcttct tcctcttcta gcctttcagt gctaccttca tctctttcag ttttcaaaa     480 tcccacagat gtggcacgga gcaaccccaa gtcaccacaa aaacctatcg ttagagtctt     540
cctgcccaac aaacagagga cagtggtacc tgcaaggtgt ggagttacag tccgagacag     600
tctaaagaaa gcactgatga tgagaggtct aatcccagag tgctgtgctg tttacagaat     660
tcaggatgga gagaagaaac caattggttg ggacactgat atttcctggc ttactggaga      720
agaattgcat gtgaagtgt tggagaatgt tccacttaca cacacaact ttgtacgaaa       780 aacgttttc accttagcat tttgtgactt ttgtcgaaag ctgcttttcc agggtttccg      840
ctgtcaaaca tgtggttata aatttcacca gcgttgtagt acagaagttc cactgatgtg      900
tgttaattat gaccaacttg atttgctgtt tgtctccaag ttctttgaac accaccaat      960 accacaggaa gaggcgtcct tagcagagac tgccctaaca tctggatcat ccccttccgc    1020
acccgcctcg gactctattg gccccaaat tctcaccagt ccgtctcctt caaaatccat    1080
tccaattcca cagcccttcc gaccagcaga tgaagatcat cgaaatcaat tgggcaacg     1140 agaccgatcc tcatcagctc ccaatgtgca tataaacaca atagaacctg tcaatattga    1200
tgacttgatt agagaccaag gatttcgtgg tgatggagga tcaaccacag gtttgtctgc    1260 tacccccct gcctcattac ctggctcact aactaacgtg aaagccttac agaaatctcc     1320
aggacctcag cgagaaagga agtcatcttc atcctcagaa gacaggaatc gaatgaaaac    1380
acttggtaga cgggactcga gtgatgattg ggagattcct gatgggcaga ttacagtggg    1440
```

```
                                          -continued acaaagaatt ggatctggat catttggaac agtctacaag ggaaagtggc atggtgatgt    1500
ggcagtgaaa atgttgaatg tgacagcacc tacacctcag cagttacaag ccttcaaaaa    1560
tgaagtagga gtactcagga aaacacgaca tgtgaatatc ctactcttca tgggctattc    1620
cacaaagcca caactggcta ttgttaccca gtggtgtgag ggctccagct tgtatcacca    1680
tctccatatc attgagacca aatttgagat gatcaaactt atagatattg cacgacagac    1740
tgcacagggc atggattact tacacgccaa gtcaatcatc cacagagacc tcaagagtaa    1800
taatatattt cttcatgaag acctcacagt aaaaataggt gattttggtc tagctacaga    1860
gaaatctcga tggagtgggt cccatcagtt tgaacagttg tctggatcca ttttgtggat    1920
ggcaccagaa gtcatcagaa tgcaagataa aaatccatac agctttcagt cagatgtata    1980
tgcatttgga attgttctgt atgaattgat gactggacag ttaccttatt caaacatcaa    2040
caacagggac cagataattt ttatggtggg acgaggatac ctgtctccag atctcagtaa    2100
ggtacggagt aactgtccaa aagccatgaa gagattaatg gcagagtgcc tcaaaaagaa    2160
aagagatgag agaccactct ttccccaaat tctcgcctct attgagctgc tggcccgctc    2220
attgccaaaa attcaccgca gtgcatcaga accctccttg aatcgggctg gtttccaaac    2280
agaggatttt agtctatatg cttgtgcttc tccaaaaaca cccatccagg caggggata    2340 tggtgcgttt cctgtccact gaaacaaatg agtgagagag ttcaggagag tagcaacaaa    2400
aggaaaataa atgaacatat gtttgcttat atgttaaatt gaataaaata ctctctttt    2460 ttttaaggtg aaccaagaa cacttgtgtg gttaaagact agatataatt tttccccaaa    2520
ctaaaattta tacttaacat tggatttta acatccaagg gttaaaatac atagacattg    2580
ctaaaaattg gcagagcctc ttctagaggc tttactttct gttccgggtt tgtatcattc    2640
acttggttat tttaagtagt aaacttcagt ttctcatgca acttttgttg ccagctatca    2700
catgtccact agggactcca gaagaagacc ctaccatgc ctgtgtttgc aggtgagaag    2760
ttggcagtcg gttagcctgg gttagataag gcaaactgaa cagatctaat ttaggaagtc    2820
agtagaattt aataattcta ttattattct taataatttt tctataacta tttctttta    2880 taacaatttg gaaatgtgg atgtctttta tttccttgaa gcaataaact aagtttcttt    2940
ttataaaaa                                                            2949

<210> SEQ ID NO 4
<211> LENGTH: 766
<212> TYPE: PRT
<213> ORGANISM: Homo sapiens

<400> SEQUENCE: 4

Met Ala Ala Leu Ser Gly Gly Gly Gly Gly Ala Glu Pro Gly Gln
1               5                   10                  15

Ala Leu Phe Asn Gly Asp Met Glu Pro Glu Ala Gly Ala Gly Ala Gly
                20                  25                  30

Ala Ala Ala Ser Ser Ala Ala Asp Pro Ala Ile Pro Glu Glu Val Trp
            35                  40                  45

Asn Ile Lys Gln Met Ile Lys Leu Thr Gln Glu His Ile Glu Ala Leu
        50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110
```

-continued

Ser Ser Ala Ser Met Asp Thr Val Thr Ser Ser Ser Ser Ser Leu
        115                 120                 125

Ser Val Leu Pro Ser Ser Leu Ser Val Phe Gln Asn Pro Thr Asp Val
130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
                180                 185                 190

Glu Cys Cys Ala Val Tyr Arg Ile Gln Asp Gly Glu Lys Lys Pro Ile
                195                 200                 205

Gly Trp Asp Thr Asp Ile Ser Trp Leu Thr Gly Glu Glu Leu His Val
                210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
                260                 265                 270

Ser Thr Glu Val Pro Leu Met Cys Val Asn Tyr Asp Gln Leu Asp Leu
                275                 280                 285

Leu Phe Val Ser Lys Phe Phe Glu His His Pro Ile Pro Gln Glu Glu
                290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
                340                 345                 350

His Arg Asn Gln Phe Gly Gln Arg Asp Arg Ser Ser Ser Ala Pro Asn
                355                 360                 365

Val His Ile Asn Thr Ile Glu Pro Val Asn Ile Asp Asp Leu Ile Arg
                370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
                420                 425                 430

Glu Asp Arg Asn Arg Met Lys Thr Leu Gly Arg Arg Asp Ser Ser Asp
                435                 440                 445

Asp Trp Glu Ile Pro Asp Gly Gln Ile Thr Val Gly Gln Arg Ile Gly
450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
                500                 505                 510

Ile Leu Leu Phe Met Gly Tyr Ser Thr Lys Pro Gln Leu Ala Ile Val
                515                 520                 525

Thr Gln Trp Cys Glu Gly Ser Ser Leu Tyr His His Leu His Ile Ile

-continued

```
                530                 535                 540
Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
                580                 585                 590

Gly Asp Phe Gly Leu Ala Thr Glu Lys Ser Arg Trp Ser Gly Ser His
                595                 600                 605

Gln Phe Glu Gln Leu Ser Gly Ser Ile Leu Trp Met Ala Pro Glu Val
    610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
                660                 665                 670

Tyr Leu Ser Pro Asp Leu Ser Lys Val Arg Ser Asn Cys Pro Lys Ala
                675                 680                 685

Met Lys Arg Leu Met Ala Glu Cys Leu Lys Lys Lys Arg Asp Glu Arg
                690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
                740                 745                 750

Thr Pro Ile Gln Ala Gly Gly Tyr Gly Ala Phe Pro Val His
                755                 760                 765
```

US 8,637,246 B2

BRAF MUTATIONS CONFERRING RESISTANCE TO BRAF INHIBITORS

This application claims the benefit under 35 U.S.C. §371 of International Application No. PCT/US2011/025645, filed Feb. 22, 2011, which claims the benefit of U.S. Provisional Application Ser. No. 61/308,275, filed Feb. 25, 2010, which are incorporated by reference herein in their entirety.

RELATED APPLICATIONS

This application claims the benefit of priority to U.S. Ser. No. 61/308,275, filed on Feb. 25, 2010. The contents of this application are incorporated herein by reference.

GOVERNMENT SUPPORT

This invention was made with Government support under Grant No. K08 CA115927, awarded by the National Institutes of Health. The Government has certain rights in the invention.

BACKGROUND OF THE INVENTION

The treatment of cancer is one of the greatest challenges in modern medicine. While chemotherapeutic agents are typically an effective means of treating or reducing the symptoms associated with cancer, in some cases, resistance to one or more chemotherapeutic agents manifests during treatment. As a result, a given chemotherapeutic agent can become ineffective in certain individuals. The molecular mechanisms responsible for the development of resistance in various types of cancer are poorly understood. Elucidation of the mechanisms that underlie resistance to specific agents is essential to discovering treatment approaches that effectively circumvent drug resistance.

SUMMARY OF THE INVENTION

The present invention pertains to mutation-mediated resistance to chemotherapeutic treatment of cancer. In specific embodiments, the present invention is directed to mutations identified in RAF polypeptides (e.g., BRAF polypeptides), and in nucleic acid molecules encoding the RAF polypeptides. These mutations confer resistance to RAF inhibitors currently in therapeutic use. The identification of these mutations allows for the development of second-generation RAF inhibitors that exhibit activity against a RAF polypeptide containing one or more mutations, such as the mutations described herein. Such second-generation RAF inhibitors are useful in many clinical and therapeutic applications, including the treatment of cancer.

Accordingly, the invention features, in a first aspect, an isolated nucleic acid molecule encoding a mutant BRAF polypeptide having a BRAF activity, wherein said mutant BRAF polypeptide comprises an amino acid sequence having at least one amino acid substitution as compared to a wild type BRAF polypeptide (SEQ ID NO: 2) or a BRAF V600E polypeptide (SEQ ID NO:4), the at least one amino acid substitution conferring resistance to one or more BRAF inhibitors on the mutant BRAF polypeptide. In certain embodiments of this aspect, the at least one amino acid substitution occurs at one or more of the following amino acid positions: A29, H72, S113, S124, P162, C194, L227, P231, C251, V291, Q329, V483, L485, T521, V528, D587, P655, S657, S683, P686, C696, L697, P722, F738, and C748. In exemplary embodiments, the at least one amino acid substitution is one or more of the following: A29V, H72N, S113I, S124F, P162H, C194*, L227F, P231T, C251F, V291F, Q329K, V483E, L485F, T521K, V528F, D587E, P655T, S657*, S683R, P686Q, P686T, C696*, L697I, P722T, F738L, and C748F.

In one embodiment of the foregoing aspect, the mutant BRAF polypeptide has one to five amino acid substitutions as compared to the wild type BRAF polypeptide or the BRAF V600E polypeptide. In exemplary embodiments, the mutant BRAF polypeptide has one amino acid substitution. In another exemplary embodiment, the mutant BRAF polypeptide is a BRAF comprising a substitution at one or more of the following amino acid positions of SEQ ID NO:2 or SEQ ID NO:4: V528, T521, and/or P686. In some embodiments of the foregoing aspects, the BRAF inhibitor is RAF-265.

The isolated nucleic acid molecules encoding mutant RAF polypeptides can be inserted into an expression vector and expressed in a host cell. Accordingly, in another aspect, the invention features an expression vector comprising a nucleic acid molecule set forth herein. In another aspect, the invention features a host cell comprising the foregoing expression vector. In another aspect, the invention features a method of producing a mutant BRAF polypeptide, comprising culturing a host cell containing an expression vector encoding a mutant BRAF polypeptide, such that a mutant BRAF polypeptide is produced by the cell.

In other embodiments, the invention features isolated mutant BRAF polypeptides, wherein the mutant BRAF polypeptides comprise an amino acid sequence having at least one amino acid substitution as compared to a wild type BRAF polypeptide (SEQ ID NO: 2) or a BRAF V600E polypeptide (SEQ ID NO:4), the at least one amino acid substitution conferring resistance to one or more BRAF inhibitors on the mutant BRAF polypeptide. In preferred embodiments, the isolated mutant BRAF polypeptides have an activity of a wild-type BRAF polypeptide. In one embodiment of the foregoing aspect, the at least one amino acid substitution occurs at one or more amino acid positions selected from the following: A29, H72, S113, S124, P162, C194, L227, P231, C251, V291, Q329, V483, L485, T521, V528, D587, P655, S657, S683, P686, C696, L697, P722, F738, and C748. In exemplary embodiments, the at least one amino acid substitution is selected from the following: A29V, H72N, S113I, S124F, P162H, C194*, L227F, P231T, C251F, V291F, Q329K, V483E, L485F, T521K, V528F, D587E, P655T, S657*, S683R, P686Q, P686T, C696*, L697I, P722T, F738L, and C748F. In some embodiments, the mutant BRAF polypeptide has one to five amino acid substitutions as compared to the wild type BRAF polypeptide or the BRAF V600E polypeptide. In exemplary embodiments, the mutant BRAF polypeptide has one amino acid substitution as compared to the wild type BRAF polypeptide. In other exemplary embodiments of the foregoing aspect, the BRAF inhibitor is RAF-265.

In another aspect, the invention features a method of identifying a compound that is useful in treating cancer, comprising providing an assay composition comprising a mutant BRAF polypeptide and a BRAF substrate, contacting the assay composition with a test compound under conditions that permit phosphorylation of the BRAF substrate in the absence of the test compound, and determining the effect of the compound on phosphorylation of the BRAF substrate, wherein downmodulation of phosphorylation of the BRAF substrate as compared to a suitable control identifies the compound as a compound that is useful in treating cancer. In some embodiments, the assay composition is a cell extract.

In another aspect, the invention features a method of identifying a compound as a second generation BRAF inhibitor, comprising providing an assay composition comprising a mutant BRAF polypeptide and a BRAF substrate, contacting the assay composition with a test compound under conditions that permit phosphorylation of the BRAF substrate in the absence of the test compound, and determining the effect of the compound on phosphorylation of the BRAF substrate, wherein downmodulation of phosphorylation of the BRAF substrate as compared to a suitable control identifies the compound as a second generation BRAF inhibitor. In some embodiments, the assay composition is a cell extract.

In another aspect, the invention features a method of identifying a compound that is useful in treating cancer, comprising providing a cell comprising a mutant BRAF polypeptide, contacting the cell with a test compound, and determining the effect of the compound on phosphorylation of a BRAF substrate, wherein downmodulation of phosphorylation of the BRAF substrate as compared to a suitable control identifies the compound as a compound that is useful in treating cancer.

In another aspect, the invention features a method of identifying a compound that is a second generation BRAF inhibitor, comprising providing a cell comprising a mutant BRAF polypeptide, contacting the cell with a test compound, and determining the effect of the compound on phosphorylation of a BRAF substrate, wherein downmodulation of phosphorylation of the BRAF substrate as compared to a suitable control identifies the compound as a second generation BRAF inhibitor.

In one embodiment of the foregoing aspects, the BRAF substrate is MEK1 or MEK2. In an exemplary embodiment, phosphorylation of MEK1 or MEK2 is determined using a phospho-specific MEK antibody. In another exemplary embodiment, phosphorylation of MEK1 or MEK2 is determined by measuring phosphorylation of myelin basic protein (MBP). In another exemplary embodiment, phosphorylation of MEK1 or MEK2 is determined by measuring phosphorylation of ERK1 or ERK2.

In another aspect, the invention features a method of identifying a compound that is useful in treating cancer, comprising providing a cell comprising a mutant BRAF polypeptide, contacting the cell with a test compound, and determining the effect of the compound on cell proliferation, wherein reduction in cell proliferation as compared to a suitable control identifies the compound as a compound that is useful in treating cancer.

In another aspect, the invention features a method of identifying a compound that is a second generation BRAF inhibitor, comprising providing a cell comprising a mutant BRAF polypeptide, contacting the cell with a test compound, and determining the effect of the compound on cell proliferation, wherein reduction in cell proliferation as compared to a suitable control identifies the compound as a second generation BRAF inhibitor.

In another aspect, the invention features a cell-based screening method for identifying a test compound as a second generation BRAF inhibitor, the method comprising contacting a host cell comprising a mutant BRAF polypeptide with a test compound, wherein sensitivity of the host cell to the test compound as compared to a suitable control identifies the compound as a second-generation BRAF inhibitor. In one embodiment, the sensitivity of the host cell to the test compound is measured using an assay selected from the group consisting of a cell proliferation assay, a cell viability assay, and a MEK phosphorylation assay, wherein a reduction in cell proliferation, cell viability, or MEK phosphorylation in the presence of the test compound identifies the compound as a second-generation BRAF inhibitor.

In another aspect, the invention provides a method of identifying a second-generation BRAF inhibitor, comprising selecting a potential drug using computer-assisted modeling with a three-dimensional crystal or solution structure of a mutant BRAF polypeptide, wherein said mutant BRAF polypeptide comprises an amino acid sequence having at least one amino acid substitution as compared to a wild type BRAF polypeptide or a BRAF V600E polypeptide, the at least one amino acid substitution conferring resistance to one or more BRAF inhibitors on the mutant BRAF polypeptide; contacting said potential drug with the mutant BRAF polypeptide; and detecting the interaction of said potential drug with the mutant BRAF polypeptide; wherein a compound that is capable of interacting with the mutant BRAF polypeptide is identified as a second-generation BRAF inhibitor. In one embodiment, the test compound is a member of a library of compounds.

In another aspect, the invention features an isolated compound that is a second-generation BRAF inhibitor or a compound that is useful in treating a cancer, wherein the compound is identified as a second-generation BRAF inhibitor or a compound that is useful in treating cancer according to a method described herein.

In another aspect, the invention features a method of inhibiting the activity of a mutant BRAF polypeptide, comprising contacting the mutant BRAF polypeptide with a compound that is a second-generation BRAF inhibitor. In preferred embodiments of the foregoing aspect, the compound further inhibits the activity of a wild-type BRAF polypeptide and/or a BRAF V600E polypeptide. In some embodiments, contacting the mutant BRAF polypeptide with the second-generation BRAF inhibitor occurs in vitro. In other embodiments, the contacting occurs in vivo. In exemplary embodiments, the contacting occurs in a subject, for example, in a subject having cancer. In some embodiments, the subject has relapsed from treatment with RAF-265. In exemplary embodiments, the cancer is a melanoma.

In another aspect, the invention features a method of treating cancer in a subject, comprising administering to the subject a compound that is a second-generation BRAF inhibitor. In exemplary embodiments, the cancer contains one or more mutations in BRAF, wherein the one or more mutations confer resistance to RAF-265 on a BRAF polypeptide. In preferred embodiments of the foregoing aspect, the compound further inhibits the activity of a wild-type BRAF polypeptide and/or a BRAF V600E polypeptide. In some embodiments, the subject has relapsed from treatment with RAF-265. In exemplary embodiments, the cancer is a melanoma.

In another aspect, the invention features a method of screening a subject having cancer for a BRAF mutation conferring resistance to treatment with a RAF inhibitor, comprising obtaining a cancer cell-containing sample from the subject, and identifying in the sample a nucleic acid molecule encoding a BRAF polypeptide containing one or more mutations with respect to a nucleic acid molecule encoding a wild-type BRAF polypeptide (SEQ ID NO:1) or a BRAF V600E polypeptide (SEQ ID NO:3), the mutations occurring at positions encoding one or more amino acids in the BRAF polypeptide selected from the group consisting of A29, H72, S113, S124, P162, C194, L227, P231, C251, V291, Q329, V483, L485, T521, V528, D587, P655, S657, S683, P686, C696, L697, P722, F738, and C748, wherein the presence of the nucleic acid molecule in the cancer cell-containing sample identifies the subject as being resistant to treatment with a RAF inhibitor. In exemplary embodiments, the nucleic acid molecule encodes a BRAF polypeptide having one or more amino acid substitutions with respect to a wild type BRAF polypeptide (SEQ ID NO:2) or a BRAF V600E polypeptide (SEQ ID NO:4) selected from the group consisting of A29V, H72N, S113I, S124F, P162H, C194*, L227F, P231T, C251F, V291F, Q329K, V483E, L485F, T521K, V528F, D587E, P655T, S657*, S683R, P686Q, P686T, C696*, L697I, P722T, F738L, and C748F. In some embodiments, the presence of the nucleic acid molecule in the cancer cell-containing sample identifies the subject as having a relatively high risk of relapse during treatment with a first generation BRAF inhibitor. In other embodiments, the presence of the nucleic acid molecule in the cancer cell-containing sample identifies the subject as being unresponsive to treatment with a first-generation BRAF inhibitor. In exemplary embodiments, the first-generation BRAF inhibitor is RAF-265. In some embodiments, the presence of the nucleic acid molecule in the cancer cell-containing sample stratifies the subject to treatment with a second generation BRAF inhibitor. In exemplary embodiments, the presence of the nucleic acid molecule in the cancer cell-containing sample is determined by a method comprising determining the sequence of a nucleic acid molecule encoding the BRAF polypeptide. In other embodiments, the presence of the nucleic acid molecule in the cancer cell-containing sample is determined by detecting a polypeptide encoded by the nucleic acid molecule using an antibody that specifically recognizes a BRAF polypeptide containing a mutation at a position selected from the group consisting of A29, H72, S113, S124, P162, C194, L227, P231, C251, V291, Q329, V483, L485, T521, V528, D587, P655, S657, S683, P686, C696, L697, P722, F738, and C748. In an exemplary embodiment, the methods described in the foregoing aspects further comprise administering a second-generation BRAF inhibitor to a subject in whom the presence of one or more mutations BRAF mutations was detected.

BRIEF DESCRIPTION OF THE DRAWINGS

FIG. 1 depicts the nucleotide sequence of wild-type human BRAF (SEQ ID NO:1) (NCBI Reference Sequence No.: NM_004333.4; gi 187608632).

FIG. 2 depicts the polypeptide sequence of wild-type human BRAF (SEQ ID NO:2) (NCBI Reference Sequence No.: NP_004324.2; gi 33188459).

FIG. 3 depicts the nucleotide sequence of human BRAF V600E (SEQ ID NO:3). The thymidine to adenosine transversion which accounts for the V600E amino acid substitution with respect to the wild-type BRAF sequence is underlined.

FIG. 4 depicts the polypeptide sequence of human BRAF V600E (SEQ ID NO:4). The V600E substitution with respect to the wild-type BRAF sequence is underlined.

FIG. 5 depicts the BRAF mutational landscape following RAF265 selection. Amino acid substitutions occurring as a result of high frequency mutations are shown.

FIG. 6 depicts the BRAF mutational landscape following PLX4720 selection. Amino acid substitutions occurring as a result of high frequency mutations are shown.

FIG. 7 depicts the structural location of three amino acid substitutions common to both the RAF265 and PLX4720 screens.

FIG. 8 depicts the results of immunoblot studies of BRAF, p-MEK1/2 and p-ERK1/2 levels following treatment with increasing concentrations of PLX4720 in cells containing BRAF-wild type, BRAF-V600E, BRAF-V600E-T521K, BRAF-V600E-V528F, or BRAF-V600E-P686Q.

DETAILED DESCRIPTION OF THE INVENTION

I. BRAF Biological Activity

The RAF protein family contains three members: BRAF, ARAF, and CRAF (also known as RAF-1). Each of the RAF proteins contains an amino-terminal regulatory domain, an activation loop, and a C-terminal kinase domain. The regulation of RAF involves phosphorylation of the regulatory and catalytic domains. Once activated, RAF molecules function as serine/threonine kinases capable of activating downstream signaling molecules by phosphorylation.

RAF is implicated in promoting cell proliferation by association with the mitogen-activated protein kinase (MAPK) signaling pathway. In particular, RAF proteins are the principle effectors of Ras-mediated signaling. Activated Ras interacts directly with RAF and recruits RAF to the cell membrane from the cytoplasm. Upon translocation to the cell membrane, Ras-bound RAF undergoes a series of phosphorylation events and conformational changes which serve to activate RAF serine/threonine kinase activity. RAF may also be activated through Ras-independent pathways involving interferon beta, protein kinase C (PKC) alpha, anti-apoptotic proteins such as Bcl-2, various scaffolding proteins, ultraviolet light, ionizing radiation, retinoids, erythropoietin, and dimerization between RAF isoforms.

Once activated, RAF mediates downstream signaling by phosphorylating the kinases MEK1 and MEK2, which contain a proline-rich sequence that enables recognition by RAF. BRAF is a far more potent activator of MEK1 and MEK2 than either ARAF or RAF-1. MEK1 and MEK2, in turn, phosphorylate and activate ERK1 and ERK2, which then translocate to the nucleus. Nuclear ERK1 and ERK2 activate transcription factors such as Elk-1, Fos, Jun, AP-1 and Myc, ultimately inducing transcription of genes involved in cell proliferation, dedifferentiation and survival, including, for example, cyclin D1, cyclin E, and cdc activator 25 phosphatase.

Upregulation of RAF signaling, resulting either from the presence of activating mutations in RAF or aberrant signaling through Ras, promotes oncogenesis by activating the foregoing signal cascade resulting in increased cell proliferation and survival. Activating mutations in RAF polypeptides, especially in BRAF, have been associated with a high frequency of human cancers. One such BRAF mutation is a single thymidine to adenosine transversion, which converts valine at amino acid 600 to glutamate. Approximately two thirds of melanoma cases harbor this oncogenic BRAF V600E mutation, which contributes to melanocyte transformation through activation of MAPK signaling. Many other types of cancer, including but not limited to colon, ovary, and thyroid cancer, likewise harbor the BRAF V600E mutation. Accordingly, targeting of RAF and, in particular, targeting of BRAF V600E, is a promising approach for cancer therapy. BRAF is an attractive target for therapy because of the high degree of specificity displayed for its MEK1 and MEK2 substrates. Several BRAF inhibitors are currently in clinical development. One such inhibitor is the compound RAF-265, which is effective against all three isoforms of RAF as well as against BRAF V600E. RAF-265 has shown promise in the clinic, indicating that targeting RAF is a viable method of cancer therapy.

As used interchangeably herein, the terms "RAF activity," "RAF biological activity," and "functional activity of RAF" include activities exerted by a RAF protein, e.g., BRAF, on a RAF-responsive cell or tissue, e.g., a cancer cell or a cancer, or on RAF target molecule, as determined in vivo or in vitro, according to standard techniques. RAF activity can be a direct activity, such as an association with a RAF target molecule e.g., MEK1 or MEK2, or phosphorylation of a RAF substrate, e.g., MEK1 or MEK2. Alternatively, a RAF activity can be an indirect activity, such as a downstream biological event mediated by interaction of the RAF protein with a RAF target molecule, e.g., MEK1 or MEK2. As RAF is in a signal transduction pathway involving MEK1 and MEK2, such downstream biological events include but are not limited to, for example, phosphorylation of MBP, phosphorylation of ERK1 or ERK2, changes in regulation of ERK1 or ERK2 target genes, and alterations in cell proliferation or viability.

II. BRAF Resistance Mutations

Although treatment of cancer with RAF inhibitors, e.g., BRAF inhibitors, is a promising therapeutic approach, patients receiving such therapy can relapse or fail to respond, and as a result the patients' disease progresses. As described herein, the present invention relates to the discovery of mutations in BRAF that confer resistance to RAF inhibitors currently in clinical development. Acquisition of such mutations in cancer cells makes patients resistant to treatment with certain RAF inhibitors. In exemplary embodiments, the invention relates to development of resistance to the RAF inhibitor RAF-265.

(A) Identification of BRAF Mutations that Confer Resistance to RAF Inhibitors

In various embodiments, the present invention relates to methods of identifying mutations in a BRAF polypeptide, or mutations in a nucleic acid molecule encoding the BRAF polypeptide, that confer resistance of the BRAF polypeptide to drugs that inhibit RAF activity. A "mutant BRAF polypeptide," as referenced herein, includes a BRAF polypeptide containing one or more mutations that confer resistance to one or more known BRAF inhibitors. In addition to the one or more mutations conferring resistance to a BRAF inhibitor, a mutant BRAF polypeptide may contain a V600E substitution. A BRAF polypeptide containing only the V600E substitution without any other mutations with respect to the wild-type BRAF polypeptide sequence is not considered to be a "mutant BRAF polypeptide" as defined herein. A "mutant BRAF nucleic acid molecule," as referenced herein, includes a nucleic acid molecule that encodes a mutant BRAF polypeptide. Nucleic acid molecules encoding BRAF polypeptides that contain one or more mutations can be created using any suitable method known in the art, including, for example, random mutagenesis or site-directed mutagenesis of a wild-type BRAF nucleic acid sequence or a BRAF V600E nucleic acid sequence, which can be conducted in *E. coli*. In exemplary embodiments, the wild-type BRAF nucleic acid sequence is a human wild-type BRAF nucleic acid sequence (SEQ ID NO:1), and the BRAF V600E nucleic acid sequence is a human BRAF V600E nucleic acid sequence (SEQ ID NO:3). The mutant BRAF nucleic acid molecules can then be screened in cells otherwise sensitive to treatment with a BRAF inhibitor to identify a nucleic acid that encodes a mutant BRAF polypeptide that is resistant to treatment with the RAF inhibitor.

A number of suitable methods can be used to screen mutant BRAF nucleic acids and mutant BRAF polypeptides for resistance to treatment with a RAF inhibitor, e.g., RAF-265. In all cases, a mutant BRAF polypeptide that is resistant to treatment with a RAF inhibitor exhibits greater BRAF activity in the presence of the RAF inhibitor than does a wild-type BRAF polypeptide or a BRAF V600E polypeptide in the presence of the RAF inhibitor. In one exemplary method, a nucleic acid molecule encoding a mutant BRAF polypeptide can be expressed in cells otherwise sensitive to treatment with a RAF inhibitor. An exemplary cell line useful for this purpose is the melanoma cell line A375. Following expression of the mutant BRAF polypeptide, the cells can be treated with a RAF inhibitor. An activity of the mutant BRAF polypeptide can then be measured and compared to the activity of a wild-type BRAF polypeptide (or a BRAF V600E polypeptide) similarly expressed and treated with the RAF inhibitor.

Activity of a BRAF polypeptide can be determined by, for example, measuring proliferation or viability of cells following treatment with the BRAF inhibitor, wherein proliferation or viability are positively correlated with BRAF activity. Cell growth, proliferation, or viability can be determined using any suitable method known in the art. In one embodiment, cell growth can be determined using well-based cell proliferation/viability assays such as MTS or Cell Titer GLo, in which cell growth in the presence of a RAF inhibitor is expressed as a percentage of that observed in untreated cells cultured in the absence of the RAF inhibitor. In certain embodiments, resistance is defined as a shift in the GI50 value of at least 2 fold, more preferably at least 3 fold, most preferably at least 4-5 fold, with respect to a suitable control. In other embodiments, resistance is defined as a GI50 value of ~1 uM). Activity of a BRAF polypeptide can also be measured by, for example, determining the relative amount of phosphorylated MEK1/2 or ERK1/2 present in the cell following treatment with the BRAF inhibitor. Activity of a wild-type or mutant BRAF polypeptide can also be determined using an in vitro phosphorylation assay, in which BRAF activity is determined by measuring the proportion of phosphorylated MEK1/2 or ERK1/2 in the assay following treatment with the BRAF inhibitor. As noted above, MEK1/2 is a substrate of BRAF, while ERK1/2 is a substrate of MEK1/2, and serves as a downstream indicator of BRAF activity. A mutant BRAF polypeptide having greater activity than a wild-type BRAF polypeptide or a BRAF V600E polypeptide following treatment with a RAF inhibitor is identified as containing a mutation that confers resistance to a RAF inhibitor. The mutation conferring resistance to a RAF inhibitor can then be identified by sequencing the nucleic acid encoding the mutant BRAF polypeptide, or by sequencing the mutant BRAF polypeptide directly.

(B) BRAF Mutations that Confer Resistance to RAF-265

In the foregoing manner, several amino acid residues of the human BRAF polypeptide were identified that, when mutated, confer resistance to the RAF inhibitor RAF-265. These amino acid residues include one or more of the following: A29, H72, S113, S124, P162, C194, L227, P231, C251, V291, Q329, V483, L485, T521, V528, D587, P655, S657, S683, P686, C696, L697, P722, F738, and C748. In certain embodiments of the invention, mutant BRAF polypeptides contain a mutation with respect to the wild-type human BRAF polypeptide sequence (or the BRAF V600E polypeptide sequence) at one or more of these amino acid residues. In related embodiments, mutant BRAF nucleic acid molecules contain a mutation with respect to the wild-type human BRAF nucleic acid sequence (or the BRAF V600E polypeptide sequence) at one or more nucleotides encoding one or more of these amino acid residues. In exemplary embodiments, mutant BRAF polypeptides featured herein contain one or more of the following resistance mutations: A29V, H72N, S113I, S124F, P162H, C194*, L227F, P231T, C251F, V291R, Q329K, V483E, L485F, T521K, V528F, D587E, P655T, S657*, S683R, P686Q, P686T, C696*, L697I, P722T, F738L, and C748F. In other exemplary embodiments, the mutant BRAF nucleic acid molecules featured herein encode a mutant BRAF polypeptide contain one or more of the following resistance mutations: A29V, H72N, S113I, S124F, P162H, C194*, L227F, P231T, C251F, V291F, Q329K, V483E, L485F, T521K, V528F, D587E, P655T, S657*, S683R, P686Q, P686T, C696*, L697I, P722T, F738L, and C748F.

The mutant BRAF nucleic acid molecules and mutant BRAF polypeptides of the invention may contain other mutations in addition to those described herein. For example, a mutant BRAF polypeptide of the invention may contain mutations at other amino acid residues in addition to one or more mutations at amino acid residues A29, H72, S113, S124, P162, C194, L227, P231, C251, V291, Q329, V483, L485, T521, V528, D587, P655, S657, S683, P686, C696, L697, P722, F738, and C748. In all cases, the mutant BRAF polypeptides of the invention have BRAF activity, and the mutant BRAF nucleic acid molecules of the invention encode polypeptides having BRAF activity. In an exemplary embodiment, a mutant BRAF molecule of the invention has a mutation at amino acid residue V600, in addition to one or more mutations at amino acid residues A29, H72, S113, S124, P162, C194, L227, P231, C251, V291, Q329, V483, L485, T521, V528, D587, P655, S657, S683, P686, C696, L697, P722, F738, and C748. In one embodiment, the mutation at V600 is an activating mutation, for example, a V600E mutation. The RAF inhibitor RAF-265 has been shown to effectively inhibit the activity of BRAF containing a V600E activating mutation. This mutation is present in a high percentage of tumors, including approximately two thirds of melanomas. The BRAF resistance mutations described herein confer resistance to RAF inhibitors such as RAF-265 upon the BRAF-V600E allele. Accordingly, patients having a tumor containing BRAF-V600E are at risk of relapse during treatment with a first-generation BRAF inhibitor such as RAF-265 due to acquiring a second BRAF mutation at any of the following sites: A29, H72, S113, S124, P162, C194, L227, P231, C251, V291, Q329, V483, L485, T521, V528, D587, P655, S657, S683, P686, C696, L697, P722, F738, and C748.

As described herein, identification of mutations in BRAF conferring resistance to BRAF inhibitors allows the design and screening of "second generation RAF inhibitors," which are effective at inhibiting a BRAF protein having one or more resistance mutations. Such second-generation RAF inhibitors are useful in many clinical and therapeutic applications, for example, in the treatment of cancer. Identification of resistance mutations in the BRAF polypeptide also allows the screening of patients having a cancer in order to determine the presence or absence of one or more BRAF resistance mutations in the cancer. Determining the presence or absence of one or more BRAF resistance mutations in a cancer allows alteration of the treatment strategy of a cancer patient. For example, identification of one or more of the BRAF resistance mutations described herein in a cancer cell-containing sample from a patient having a cancer can be used to stratify the patient to treatment with a second-generation RAF inhibitor. Likewise, identification of one or more of the BRAF resistance mutations described herein in a cancer cell-containing sample from a patient having a cancer can be used to stratify the patient to treatment with a MEK inhibitor. Identification of BRAF resistance mutations also allows the screening and identification of patients having a high risk of relapse or lack of response to treatment with certain RAF inhibitors.

III. Methods for Identifying Second-Generation BRAF Inhibitors

Identification of BRAF resistance mutations allows the development and/or identification of "second-generation RAF inhibitors." As used herein, a second-generation RAF inhibitor is an agent that effectively inhibits the activity of a RAF polypeptide, e.g., a BRAF polypeptide, containing one or more mutations described herein. A second-generation RAF inhibitor may or may not inhibit the activity of a wild-type RAF polypeptide in addition to a mutant RAF polypeptide. In a preferred embodiment, a second-generation RAF inhibitor inhibits the activity of a BRAF V600E polypeptide (SEQ ID NO:4), as well as a BRAF V600E polypeptide additionally having one or more of the resistance mutations described herein. In an exemplary embodiment, a second-generation RAF inhibitor inhibits the activity of a BRAF polypeptide containing mutations at one or more of the following amino acid residues: A29, H72, S113, S124, P162, C194, L227, P231, C251, V291, Q329, V483, L485, T521, V528, D587, P655, S657, S683, P686, C696, L697, P722, F738, and C748.

Accordingly, the present invention provides methods for identifying a test compound as a second-generation RAF inhibitor. In one embodiment, a compound can be identified as a second-generation RAF inhibitor by determining the relative RAF activity of a mutant BRAF polypeptide in the presence or absence of the compound, with respect to a non-mutant BRAF polypeptide (e.g., a wild-type BRAF polypeptide, or a BRAF V600E polypeptide). When in the presence of a compound that is a second-generation RAF inhibitor, a mutant BRAF polypeptide has a lower level of RAF activity than in the absence of the compound. When in the presence of a compound that is not a second-generation RAF inhibitor, a mutant BRAF polypeptide has an equivalent or higher level of RAF activity than in the absence of the compound. In certain embodiments, RAF activity can be measured in an in vitro assay using recombinant BRAF polypeptides. In other embodiments, RAF activity can be measured in an in vivo assay using cultured cells or experimental animals expressing BRAF polypeptides.

Any indicator of BRAF activity is suitable for determining whether or not a compound is a second-generation RAF inhibitor. In an exemplary embodiment, BRAF activity is determined by measuring phosphorylation of the RAF substrate MEK1/2, wherein a decrease in MEK1/2 phosphorylation indicates a decrease in RAF activity. In one embodiment, MEK1/2 phosphorylation is measured in a cell or cell extract. In an alternate embodiment, MEK1/2 phosphorylation is measured in an in vitro phosphorylation assay using purified or recombinant proteins. Methods of detecting MEK1/2 phosphorylation known in the art are suitable for measuring MEK1/2 phosphorylation as an indication of the activity of a BRAF polypeptide or a mutant BRAF polypeptide. Such methods include, but are not limited to, Western blot and mass spectroscopy. In certain embodiments, a MEK1/2 phosphorylation assay can be performed in vitro using recombinant proteins. In other embodiments, an MEK1/2 phosphorylation assay can be performed in vivo using cultured cells or experimental animals.

In another exemplary embodiment, BRAF activity is determined by measuring phosphorylation of the MEK substrate ERK1/2, wherein a decrease in ERK1/2 phosphorylation indicates a decrease in BRAF activity. In one embodiment, ERK1/2 phosphorylation is measured in a cell or cell extract. In an alternate embodiment, ERK1/2 phosphorylation is measured in an in vitro phosphorylation assay using purified or recombinant proteins. Methods of detecting ERK1/2 phosphorylation known in the art are suitable for measuring ERK1/2 phosphorylation as an indication of the activity of a BRAF polypeptide or a mutant BRAF polypeptide. Such methods include, but are not limited to, Western blot and mass spectroscopy. In certain embodiments, an ERK1/2 phosphorylation assay can be performed in vitro using recombinant proteins. In other embodiments, an ERK1/2 phosphorylation assay can be performed in vivo using cultured cells or experimental animals.

In one embodiment, a host cell expressing a mutant BRAF polypeptide is used in the identification of a second-generation RAF inhibitor, wherein the sensitivity of the host cell to a test compound identifies the test compound as a second-generation RAF inhibitor. As used herein, the term "sensitivity of the host cell to a test compound" is intended to mean that the test compound has a measurable effect on one or more parameters including cell growth, cell proliferation, cell viability and/or intracellular signal transduction (e.g., signal transduction mediated by BRAF as evidenced by, for example, phosphorylation of one or more BRAF substrates, such as MEK1/2, or one or more downstream signaling molecules, such as ERK1/2).

A compound can be identified as a second-generation RAF inhibitor by determining the viability or proliferation rate of cells expressing a mutant BRAF polypeptide in the presence or absence of the compound. The cell line used in such an assay should be sensitive to a RAF inhibitor when the cell line expresses a wild-type BRAF polypeptide, and should be resistant to the RAF inhibitor (i.e., a first-generation RAF inhibitor) when the cell line expresses a mutant BRAF polypeptide. An exemplary cell line useful for identification of a second-generation RAF inhibitor is the melanoma cell line A375. A375 cells are sensitive to the RAF inhibitor RAF-265 when expressing a wild-type BRAF polypeptide, but are resistant to RAF-265 when expressing a mutant BRAF polypeptide, for example, a BRAF polypeptide containing one or more of the following resistance mutations: A29V, H72N, S113I, S124F, P162H, C194*, L227F, P231T, C251F, V291F, Q329K, V483E, L485F, T521K, V528F, D587E, P655T, S657*, S683R, P686Q, P686T, C696*, L697I, P722T, F738L, and C748F.

When in the presence of a compound that is a second-generation RAF inhibitor, a cell line expressing a mutant BRAF polypeptide has a lower viability or proliferation rate than in the absence of the compound. When in the presence of a compound that is not a second-generation RAF inhibitor, a cell line expressing a mutant BRAF polypeptide has an equivalent or higher viability or proliferation rate than in the absence of the compound. Methods of measuring cell viability and/or proliferation rate known in the art are suitable for determining the sensitivity of a cell line expressing a BRAF polypeptide or a mutant BRAF polypeptide to a test compound. Such methods include, but are not limited to, measurement of Trypan blue exclusion, metabolism of tetrazolium compounds, tritiated thymidine incorporation, BrdU incorporation, glucose uptake, ATP concentration, and level of apoptosis. In one embodiment, cell proliferation can be determined using well-based cell proliferation/viability assays such as MTS or Cell Titer GLo. In certain embodiments, sensitivity is defined as a shift in the GI50 value of at least 2 fold, more preferably at least 3 fold, most preferably at lease 4-5 fold, with respect to a suitable control.

Accordingly, in one embodiment, the invention provides a method of identifying a compound that is a second generation RAF inhibitor, comprising providing an assay composition comprising a BRAF substrate and a BRAF polypeptide having one or more mutations with respect to a wild-type BRAF polypeptide (or with respect to a BRAF V600E polypeptide), contacting the assay composition with a test compound under conditions that permit phosphorylation of the BRAF substrate in the absence of the test compound, and determining the effect of the compound on phosphorylation of the BRAF substrate, wherein downmodulation of phosphorylation of the BRAF substrate as compared to a suitable control identifies the compound as a second generation RAF inhibitor. A compound identified in this way is a compound useful for treating a cancer, e.g., a cancer in which a mutant RAF polypeptide has been detected. A BRAF polypeptide useful in the foregoing methods is a BRAF polypeptide containing one or more mutations which confer resistance to the RAF inhibitor RAF-265, e.g., a BRAF polypeptide containing one or more of the mutations described herein. A BRAF substrate useful in the foregoing methods is, for example, MEK1/2. A decrease, reduction, or downmodulation of MEK1/2 phosphorylation is an indication that the compound is a RAF inhibitor. Likewise, a downstream RAF signaling molecule useful in the foregoing methods is, for example, ERK1/2. A decrease, reduction, or downmodulation of ERK1/2 phosphorylation is an indication that the compound is a RAF inhibitor. The foregoing methods can be performed in vitro wherein the BRAF polypeptides and the BRAF substrates are isolated or purified proteins. The foregoing methods can also be performed in vitro wherein the BRAF polypeptides and the BRAF substrates are components of a cell extract. In this embodiment, the assay composition is a cell extract. A suitable control is any control that would be apparent to a skilled person performing the method, and includes, for example, a similar or identical assay composition not treated with a test compound or treated with a control compound, or an analogous assay composition or cell extract comprising a "wild-type" BRAF polypeptide, or a BRAF V600E polypeptide.

In another embodiment, the invention provides a method of identifying a compound that is a second generation RAF inhibitor, comprising providing a cell comprising a mutant BRAF polypeptide, contacting the cell with a test compound, and determining the effect of the compound on MEK1/2 phosphorylation, ERK1/2 phosphorylation, or cell proliferation, wherein a decrease, reduction, or downmodulation of MEK1/2 phosphorylation, ERK1/2 phosphorylation or cell proliferation as compared to an appropriate control identifies the compound as a second generation RAF inhibitor. A compound identified in this way is a compound useful for treating a cancer, e.g., a cancer in which a mutant BRAF polypeptide has been detected. A suitable control is any control that would be apparent to a skilled person performing the method, and includes, for example, a similar or identical cell not treated with a test compound or treated with a control compound, or an analogous cell or cell extract in which recombinant, "wild-type" BRAF, or BRAF V600E, was expressed.

In one embodiment, the test compound used in the foregoing methods is a RAF inhibitor that inhibits a biological activity of a wild type RAF polypeptide, e.g., a BRAF polypeptide. In addition or alternatively, the test compound used in the foregoing methods is a RAF inhibitor that inhibits the activity of a BRAF V600E polypeptide. In one embodiment, RAF inhibitors that may be used as test compounds to determine if they are second generation RAF inhibitors include PLX4032, PLX5568, XL281, and the imidazole-2-carboxamide derivatives described in US2008/0108615, the entire contents of which are incorporated herein by reference.

In another embodiment, the test compound is a member of a library of test compounds. A "library of test compounds" refers to a panel comprising a multiplicity of test compounds. An approach for the synthesis of molecular libraries of small organic molecules has been described (Carell et al. (1994). *Angew. Chem. Int. Ed. Engl.* 33:2059; Carell et al. (1994) Angew. *Chem. Int. Ed. Engl.* 33:2061). The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145). Other exemplary methods for the synthesis of molecular libraries can be found in the art, for example in: Erb et al. (1994). *Proc. Natl. Acad. Sci. USA* 91:11422; Horwell et al. (1996) *Immunopharmacology* 33:68-; and in Gallop et al. (1994); *J. Med. Chem.* 37:1233-. Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner USP '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310). In still another embodiment, the combinatorial polypeptides are produced from a cDNA library. Exemplary compounds that can be screened for activity include, but are not limited to, peptides, nucleic acids, carbohydrates, small organic molecules, and natural product extract libraries.

Second generation RAF inhibitors can also be rationally designed based on the structure of BRAF alleles containing one or more of the resistance mutations described herein. As described herein, residues of BRAF that confer resistance to RAF inhibitors are located in the same region of BRAF bound by the first-generation RAF inhibitor RAF-265. Identification of BRAF mutant alleles conferring resistance to RAF inhibitors allows comparison between the structure of the mutant alleles and the wild-type BRAF, or to BRAF V600E. Knowledge of the altered structural features that confer resistance to first-generation RAF inhibitors allows rational design and construction of ligands, including inhibitors, that will bind and inhibit the mutant alleles. Such inhibitors can be designed such that they bind both BRAF mutant alleles, BRAF V600E not containing a secondary mutation described herein, and wild-type BRAF. Inhibitors designed to bind a BRAF allele containing one or mutations described herein are second-generation RAF inhibitors. The ability of such rationally designed inhibitors to inhibit a biological activity of a mutant BRAF polypeptide can be confirmed using the in vitro and/or in vivo assays described herein.

The structure of a BRAF polypeptide containing one or more of the resistance mutations described herein can be determined by computer-assisted modeling, or by determining the crystal or solution structure of the mutant BRAF polypeptide. Any suitable method known in the art can be used to determine the structure of a mutant BRAF polypeptide.

Exemplary computer-assisted modeling methods include the use of software programs such as PYMOL, CAVITY (described in J. Comp. Aided. Mol. Des. (1990) 4:337-354 (incorporated herein by reference)) and Discovery Studio® (Accelrys, San Diego, Calif.). Additional techniques useful for computer-assisted molecular modeling are described in J BUON. (2007) 12 Suppl 1:S101-18 (incorporated herein by reference). Computer-based analysis of a protein with a known structure can also be used to identify molecules which will bind to the protein. Such methods rank molecules based on their shape complementary to a receptor site. For example, using a 3-D database, a program such as DOCK can be used to identify molecules which will bind to XBP-1, IRE-1 alpha, and/or EDEM. See DesJarlias et al. (1988) J. Med. Chem. 31:722; Meng et al. (1992) J. Computer Chem. 13:505; Meng et al. (1993) Proteins 17:266; Shoichet et al. (1993) Science 259:1445. In addition, the electronic complementarity of a molecule to a targeted protein can also be analyzed to identify molecules which bind to the target. This can be determined using, for example, a molecular mechanics force field as described in Meng et al. (1992) J. Computer Chem. 13:505 and Meng et al. (1993) Proteins 17:266. Other programs which can be used include CLIX which uses a GRID force field in docking of putative ligands (see, for example, Lawrence et al. (1992) Proteins 12:31; Goodford et al. (1985) J. Med. Chem. 28:849; and Boobbyer et al. (1989) J. Med. Chem. 32:1083, incorporated by reference in their entirety).

Crystallization can be performed by any crystallization method including, but not limited to batch, dialysis and vapor diffusion (e.g., sitting drop and hanging drop) methods. Micro, macro and/or streak seeding of crystals can also be performed to facilitate crystallization. Crystals comprising BRAF mutant alleles can be formed by a variety of different methods known in the art. For example, crystallizations can be performed by batch, dialysis, and vapor diffusion (sitting drop and hanging drop) methods. A detailed description of basic protein crystallization setups can be found in McRee, D., *Practical Protein Crystallography*, $2^{nd}$ Ed. (1999), Academic Press Inc. Further descriptions regarding performing crystallization experiments are provided in Stevens et al. (2000) *Curr. Opin. Struct. Biol.:* 10(5):558-63, and U.S. Pat. Nos. 6,296,673; 5,419,278; and 5,096,676, the entire contents of which are incorporated herein by reference. Such crystals can be used to perform X-ray or neutron diffraction analysis in order to determine the three-dimensional structure of BRAF mutant alleles. A solution structure of a BRAF polypeptide or mutant BRAF polypeptide can be identified using nuclear magnetic resonance spectroscopy using techniques known in the art. Suitable methods for polypeptide structure determination by X-Ray crystallography or NMR spectroscopy are described in Brunger et al., (1998) "Crystallography & NMR system (CNS): A new software system for macromolecular structure determination," Acta Crystallogr D54, 905-921; Brunger et al. (1987) "Solution of a Protein Crystal Structure With a Model Obtained From NMR Interproton Distance Restraints," Science 235, 1049-1053; Drenth, "Principles of Protein X-ray Crystallography," (1994), Springer-Verlag. pp. 1-19; and Narula et al. (1995) "Solution structure of the C-terminal SH2 domain of the human tyrosine kinase Syk complexed with a phosphotyrosine pentapeptide," Structure 3, 1061-1073, incorporated herein by reference in their entirety. Upon identification of the crystal or solution structure of a mutant RAF polypeptide, inhibitors of the mutant BRAF polypeptide can be identified using the computer assisted modeling approaches described above.

Second-generation RAF inhibitors identified by the foregoing methods are useful for treating a disease or condition associated with expression of a wild-type and/or mutant RAF polypeptide. For example, second-generation RAF inhibitors are useful for treating a cancer in a subject, particularly a cancer in which a mutant BRAF polypeptide has been identified. In an exemplary embodiment, second-generation RAF inhibitors are useful for treating a cancer containing a BRAF polypeptide having a mutation at one or more of the following amino acid residues: A29, H72, S113, S124, P162, C194, L227, P231, C251, V291, Q329, V483, L485, T521, V528, D587, P655, S657, S683, P686, C696, L697, P722, F738, and C748. In a related embodiment, second-generation RAF inhibitors are useful for treating a cancer containing a BRAF polypeptide having one or more of the following mutations: A29V, H72N, S113I, S124F, P162H, C194*, L227F, P231T, C251F, V291F, Q329K, V483E, L485F, T521K, V528F, D587E, P655T, S657*, S683R, P686Q, P686T, C696*, L697I, P722T, F738L, and C748F.

IV. Isolated Nucleic Acid Molecules

The present invention concerns polynucleotides or nucleic acid molecules relating to the BRAF gene and its respective gene product. These polynucleotides or nucleic acid molecules are isolatable and purifiable from mammalian cells. In particular aspects of the invention, the isolated BRAF nucleic acid molecules described herein comprise one or more mutations conferring resistance to a BRAF inhibitor. A "mutant BRAF nucleic acid molecule," as referenced herein, includes a BRAF nucleic acid molecule that encodes a mutant BRAF polypeptide, i.e., a BRAF polypeptide containing one or more mutations that confer resistance to one or more known BRAF inhibitors.

It is contemplated that an isolated and purified BRAF nucleic acid molecule, e.g., a mutant BRAF nucleic acid molecule, can take the form of RNA or DNA. As used herein, the term "RNA transcript" refers to an RNA molecule that is the product of transcription from a DNA nucleic acid molecule. Such a transcript can encode for one or more polypeptides.

As used in this application, the term "polynucleotide" refers to a nucleic acid molecule, RNA or DNA, that has been isolated, such as being free of total genomic nucleic acid. Therefore, a "polynucleotide encoding BRAF" refers to a nucleic acid segment that contains BRAF coding sequences, yet is isolated away from, or purified and free of, total genomic DNA and proteins. When the present application refers to the function or activity of a BRAF-encoding polynucleotide or nucleic acid, it is meant that the polynucleotide encodes a molecule that is capable of performing an activity of a wild-type BRAF polypeptide, for example, phosphorylation of the MEK1 or MEK2 substrates.

The term "cDNA" is intended to refer to DNA prepared using RNA as a template. The advantage of using a cDNA, as opposed to genomic DNA or an RNA transcript is stability and the ability to manipulate the sequence using recombinant DNA technology (See Sambrook, 1989; Ausubel, 1996). There can be times when the full or partial genomic sequence is preferred. Alternatively, cDNA can be advantageous because it represents coding regions of a polypeptide and eliminates introns and other regulatory regions.

It also is contemplated that a given BRAF-encoding nucleic acid or BRAF gene from a given cell may be represented by natural variants or strains that have slightly different nucleic acid sequences but, nonetheless, encode an active BRAF polypeptide. In a preferred embodiment, the active BRAF polypeptide is an active human BRAF polypeptide. In particularly preferred embodiments, the active BRAF polypeptide is a mutant BRAF polypeptide that has an activity of a wild-type BRAF polypeptide, but which is resistant to one or more known BRAF inhibitors. Consequently, certain aspects of the present invention encompass derivatives of BRAF with minimal amino acid changes, but that possess the same biological function.

The term "gene" is used for simplicity to refer to a functional protein, polypeptide, or peptide-encoding unit. As will be understood by those in the art, this functional term includes genomic sequences, cDNA sequences, and smaller engineered gene segments that express, or can be adapted to express, proteins, polypeptides, domains, fusion proteins, and mutant proteins. The nucleic acid molecule encoding BRAF can comprise a contiguous nucleic acid sequence of the following lengths: at least about 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 10100, 10200, 10300, 10400, 10500, 10600, 10700, 10800, 10900, 11000, 11100, 11200, 11300, 11400, 11500, 11600, 11700, 11800, 11900, 12000 or more nucleotides, nucleosides, or base pairs. Such sequences can be identical or complementary to, for example, SEQ ID NO:1, or a fragment thereof.

Various embodiments of the invention relate to genetic mutations in BRAF. As used herein, a mutation refers to an addition, deletion, or substitution of a single nucleotide at a site in a BRAF nucleic acid molecule. In an exemplary embodiment, a mutant BRAF nucleic acid molecule contains one or more mutations that confer resistance to a particular therapy, such as a BRAF inhibitor, e.g., RAF-265. In a related embodiment, a mutant BRAF nucleic acid molecule contains one or more mutations such that the mutant BRAF nucleic acid molecule encodes a mutant BRAF polypeptide, wherein the mutant BRAF polypeptide contains one or more mutations that confer resistance to a particular therapy, such as a BRAF inhibitor, e.g., RAF-265. Thus, in particular aspects of the invention, an alteration in a sequence results in a change that affects the properties of a polypeptide encoded by the sequence such that at least some resistance to therapy, such as therapy with a BRAF inhibitor, occurs as a result.

"Isolated substantially away from other coding sequences" means that the gene of interest forms part of the coding region of the nucleic acid segment, and that the segment does not contain large portions of naturally-occurring coding nucleic acid, such as large chromosomal fragments or other functional genes or cDNA coding regions. Of course, this refers to the nucleic acid segment as originally isolated, and does not exclude genes or coding regions later added to the segment by human manipulation.

In particular embodiments, the invention concerns isolated nucleic acid segments and recombinant vectors incorporating DNA sequences that encode mutant BRAF polypeptides or peptides that include within its amino acid sequence a contiguous amino acid sequence in accordance with, or essentially corresponding to mutant BRAF polypeptides. In exemplary embodiments, the invention concerns isolated DNA segments and recombinant vectors incorporating DNA sequences that encode a BRAF protein, polypeptide or peptide that includes within its amino acid sequence a contiguous amino acid sequence of a BRAF polypeptide comprising one or more mutations that confer resistance to a BRAF inhibitor. In certain embodiments, the one or more mutations occur at positions A29, H72, S113, S124, P162, C194, L227, P231, C251, V291, Q329, V483, L485, T521, V528, D587, P655, S657, S683, P686, C696, L697, P722, F738, and C748. In other embodiments, the one or more mutations include the following: A29V, H72N, S113I, S124F, P162H, C194*, L227F, P231T, C251F, V291F, Q329K, V483E, L485F, T521K, V528F, D587E, P655T, S657*, S683R, P686Q, P686T, C696*, L697I, P722T, F738L, and C748F.

The nucleic acid segments used in the present invention, regardless of the length of the coding sequence itself, can be combined with other DNA or RNA sequences, such as promoters, polyadenylation signals, additional restriction enzyme sites, multiple cloning sites, other coding segments, and the like, such that their overall length can vary considerably. It is therefore contemplated that a nucleic acid fragment of almost any length can be employed, with the total length preferably being limited by the ease of preparation and use in the intended recombinant DNA protocol.

It is contemplated that the nucleic acid constructs of the present invention encode a BRAF polypeptide or a mutant BRAF polypeptide. A "heterologous" sequence refers to a sequence that is foreign or exogenous to the remaining sequence. A heterologous gene refers to a gene that is not found in nature adjacent to the sequences with which it is now placed.

In a non-limiting example, one or more nucleic acid constructs can be prepared that include a contiguous stretch of nucleotides identical to or complementary to all or part of a BRAF gene. A nucleic acid construct can comprise at least 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 11,000, 12,000, 13,000, 14,000, 15,000, 20,000, 30,000, 50,000, 100,000, 250,000, about 500,000, 750,000, to about 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges," as used herein, means any length or range including or between the quoted values (i.e., all integers including and between such values). Non-limiting examples of intermediate lengths include about 11, about 12, about 13, about 16, about 17, about 18, about 19, etc.; about 21, about 22, about 23, etc.; about 31, about 32, etc.; about 51, about 52, about 53, etc.; about 101, about 102, about 103, etc.; about 151, about 152, about 153, about 97001, about 1,001, about 1002, about 50,001, about 50,002, about 750,001, about 750,002, about 1,000,001, about 1,000, 002, etc. Non-limiting examples of intermediate ranges include about 3 to about 32, about 150 to about 500,001, about 3,032 to about 7,145, about 5,000 to about 15,000, about 20,007 to about 1,000,003, etc.

Certain embodiments of the present invention concern various nucleic acids, including vectors, promoters, therapeutic nucleic acids, and other nucleic acid elements involved in transformation and expression in cells. In certain aspects, a nucleic acid comprises a wild-type or a mutant nucleic acid. In particular aspects, a nucleic acid encodes for or comprises a transcribed nucleic acid.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C).

The term "nucleic acid" encompasses the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length. A "gene" refers to coding sequence of a gene product, as well as introns and the promoter of the gene product. In addition to the BRAF gene, other regulatory regions such as enhancers for BRAF are contemplated as nucleic acids for use with compositions and methods of the claimed invention.

These definitions generally refer to a single-stranded molecule, but in specific embodiments will also encompass an additional strand that is partially, substantially or fully complementary to the single-stranded molecule. Thus, a nucleic acid can encompass a double-stranded molecule or a triple-stranded molecule that comprises one or more complementary strand(s) or "complement(s)" of a particular sequence comprising a molecule. As used herein, a single stranded nucleic acid can be denoted by the prefix "ss", a double stranded nucleic acid by the prefix "ds", and a triple stranded nucleic acid by the prefix "ts."

A nucleic acid can be made by any technique known to one of ordinary skill in the art, for example, by chemical synthesis, or by enzymatic production or biological production. Non-limiting examples of a synthetic nucleic acid (e.g., a synthetic BRAF primer that facilitates identification of a mutation conferring resistance to a BRAF inhibitor), include a nucleic acid made by in vitro chemical synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotides can be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid includes one produced by enzymes in an amplification reactions such as PCR (see for example, U.S. Pat. Nos. 4,683,202 and 4,682,195, each incorporated herein by reference), or one produced by synthesis of oligonucleotides, as described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 1989, incorporated herein by reference).

A nucleic acid can be purified on polyacrylamide gels, cesium chloride centrifugation gradients, or by any other means known to one of ordinary skill in the art as part of assessment for a mutation that confers resistance to BRAF (see for example, Sambrook et al., 1989, incorporated herein by reference). In preferred aspects, a nucleic acid is a pharmacologically acceptable nucleic acid. Pharmacologically acceptable compositions are known to those of skill in the art, and are described herein.

In certain aspects, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has

V. Expression Vectors and Host Cells

The present invention encompasses expression vector compositions and the use of such vectors to encode for a BRAF polypeptide, e.g., a mutant BRAF polypeptide, as well as host cell compositions into which such expression vectors have been introduced. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., 1989 and Ausubel et al., 1996, both incorporated herein by reference.

The term "expression vector" or "expression construct" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors can contain nucleic acid sequences that serve other functions as well and are described infra.

1. Promoters and Enhancers

A "promoter" is a control sequence that is a region of a nucleic acid sequence at which initiation and rate of transcription are controlled. It can contain genetic elements at which regulatory proteins and molecules can bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter can be one naturally associated with a gene or sequence, as can be obtained by isolating the 5' non-coding sequences located upstream of the coding segment and/or exon. Such a promoter can be referred to as "endogenous." Similarly, an enhancer can be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers can include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression.

Naturally, it will be important to employ a promoter and/or enhancer that effectively directs the expression of the nucleic acid segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed can be constitutive, tissue-specific, inducible, and/or useful under the appropriate conditions to direct high level expression of the introduced DNA segment. The promoter can be heterologous or exogenous, for example, a non-BRAF promoter with respect to BRAF encoding sequence. In some examples, a prokaryotic promoter is employed for use with in vitro transcription of a desired sequence. Prokaryotic promoters for use with many commercially available systems include T7, T3, and Sp6.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements. In certain embodiments of the invention, the use of internal ribosome entry sites (IRES) elements are used to create multigene, or polycistronic, messages.

3. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference). "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences can require donor and/or acceptor splicing sites to ensure proper processing of the transcript for protein expression (see, for example, Chandler et al., 1997, herein incorporated by reference).

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

6. Polyadenylation Signals

For expression, particularly eukaryotic expression, one will typically include a polyadenylation signal to effect proper polyadenylation of the transcript. The nature of the polyadenylation signal is not believed to be crucial to the successful practice of the invention, and/or any such sequence can be employed. Preferred embodiments include the SV40 polyadenylation signal and/or the bovine growth hormone polyadenylation signal, convenient and/or known to function well in various target cells. Polyadenylation can increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the invention, the cells containing a nucleic acid construct of the present invention can be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) can be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

9. Host Cells

As used herein, the terms "cell," "cell line," and "cell culture" may be used interchangeably. A cell comprising a BRAF polynucleotide, either mutated or wild-type, can be employed in the invention. All of these terms also include their progeny, which refers to any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. A "recombinant host cell" refers to a host cell that carries a recombinant nucleic acid, i.e. a nucleic acid that has been manipulated in vitro or that is a replicated copy of a nucleic acid that has been so manipulated.

A host cell can be derived from prokaryotes or eukaryotes, depending upon whether the desired result is replication of the vector, expression of part or all of the vector-encoded nucleic acid sequences, or production of infectious viral particles. Numerous cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE™ Competent Cells and Solopack™ Gold Cells (Strategene®, La Jolla). Alternatively, bacterial cells such as E. coli LE392 could be used as host cells for phage viruses.

A preferred eukaryotic host cell of the invention is the melanoma cell line A375, wherein the cell has been transformed with an expression vector encoding a BRAF polypeptide, e.g., a mutant BRAF polypeptide of the invention.

10. Expression Systems

Numerous expression systems exist that comprise at least a part or all of the compositions discussed above. Prokaryotic- and/or eukaryotic-based systems can be employed for use with the present invention to produce BRAF nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MaxBac™ 2.0 from Invitrogen™ and BacPack™ Baculovirus Expression System from Clontech™.

Other examples of expression systems include Stratagene's Complete Control Inducible Mammalian Expression System, which involves a synthetic ecdysone-inducible receptor, or its pET Expression System, an E. coli expression system. Another example of an inducible expression system is available from Invitrogen, which carries the T-Rex™ (tetracycline-regulated expression) System, an inducible mammalian expression system that uses the full-length CMV promoter. The Tet-On™ and Tet-Off™ systems from Clontech™ can be used to regulate expression in a mammalian host using tetracycline or its derivatives. The implementation of these systems is described in Gossen et al., 1992 and Gossen et al., 1995, and U.S. Pat. No. 5,650,298, all of which are incorporated by reference.

Invitrogen also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

VI. Isolated Polypeptide Molecules

Another aspect of the invention pertains to isolated and/or purified BRAF proteins, and biologically active portions thereof. In particular aspects of the invention, the BRAF polypeptides described herein comprise one or more mutations conferring resistance to a BRAF inhibitor. A "mutant BRAF polypeptide", as referenced herein, includes a BRAF polypeptide containing one or more mutations that confer resistance to one or more known BRAF inhibitors.

An "isolated" or "purified" protein or biologically active portion thereof is substantially free of cellular material when produced by recombinant DNA techniques, or chemical precursors or other chemicals when chemically synthesized. The language "substantially free of cellular material" includes preparations of BRAF proteins in which the protein is separated from cellular components of the cells in which it is naturally or recombinantly produced. In one embodiment, the language "substantially free of cellular material" includes preparations of BRAF protein having less than about 30% (by dry weight) of non-BRAF protein (also referred to herein as a "contaminating protein"), more preferably less than about 20% of non-BRAF protein, still more preferably less than about 10% of non-BRAF protein, and most preferably less than about 5% of non-BRAF protein. When the BRAF protein or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of BRAF protein in which the protein is separated from chemical precursors or other chemicals which are involved in the synthesis of the protein. In one embodiment, the language "substantially free of chemical precursors or other chemicals" includes preparations of BRAF protein having less than about 30% (by dry weight) of chemical precursors or non-BRAF chemicals, more preferably less than about 20% chemical precursors or non-BRAF chemicals, still more preferably less than about 10% chemical precursors or non-BRAF chemicals, and most preferably less than about 5% chemical precursors or non-BRAF chemicals.

Biologically active portions of a BRAF protein include peptides comprising amino acid sequences derived from the amino acid sequence of a BRAF protein, e.g., the amino acid sequence shown in SEQ ID NO:2, or the amino acid sequence of a protein homologous to a BRAF protein, which include fewer amino acids than a full length BRAF protein or the full length protein which is homologous to a BRAF protein, and exhibit at least one activity of a BRAF protein. Typically, biologically active portions (peptides, e.g., peptides which are, for example, 5, 10, 15, 20, 30, 35, 36, 37, 38, 39, 40, 50, 100, 200, 300, 400, 500, 600, 700 or more amino acids in length) comprise a domain or motif with at least one activity of a BRAF protein. Moreover, other biologically active portions, in which other regions of the protein are deleted, can be prepared by recombinant techniques and evaluated for one or more of the activities described herein. Preferably, the biologically active portions of a BRAF protein include one or more selected domains/motifs or portions thereof having biological activity. In preferred embodiments, biologically active portions of a BRAF protein comprise one or more mutations with respect to a wild-type BRAF sequence, wherein said one or more mutations, when present in a full-length mutant BRAF polypeptide, confer resistance of the mutant BRAF polypeptide to known BRAF inhibitors. In exemplary embodiments, the mutations occur at amino acids corresponding to one or more of the following positions in a wild-type BRAF protein: A29, H72, S113, S124, P162, C194, L227, P231, C251, V291, Q329, V483, L485, T521, V528, D587, P655, S657, S683, P686, C696, L697, P722, F738, and C748. In a related embodiment, the mutations include one or more of the following BRAF residues: A29V, H72N, S113I, S124F, P162H, C194*, L227F, P231T, C251F, V291F, Q329K, V483E, L485F, T521K, V528F, D587E, P655T, S657*, S683R, P686Q, P686T, C696*, L697I, P722T, F738L, and C748F.

BRAF proteins are preferably produced by recombinant DNA techniques. For example, a nucleic acid molecule encoding the protein is cloned into an expression vector (as described above), the expression vector is introduced into a host cell (as described above) and the BRAF protein is expressed in the host cell. The BRAF protein can then be isolated from the cells by an appropriate purification scheme using standard protein purification techniques. Alternative to recombinant expression, a BRAF protein, polypeptide, or peptide can be synthesized chemically using standard peptide synthesis techniques. Moreover, a native BRAF protein and/or a mutant BRAF protein can be isolated from cells (e.g., cancer cells), for example using an anti-BRAF antibody, which can be produced by standard techniques utilizing a BRAF protein or fragment thereof of this invention.

The invention also provides BRAF chimeric or fusion proteins. As used herein, a BRAF "chimeric protein" or "fusion protein" comprises a BRAF polypeptide operatively linked to a non-BRAF polypeptide. A "BRAF polypeptide" refers to a polypeptide having an amino acid sequence corresponding to a BRAF protein, whereas a "non-BRAF polypeptide" refers to a polypeptide having an amino acid sequence corresponding to a protein which is not substantially homologous to the BRAF protein, e.g., a protein which is substantially different from the BRAF protein, which does not display a BRAF activity and which is derived from the same or a different organism. Within the fusion protein, the term "operatively linked" is intended to indicate that the BRAF polypeptide and the non-BRAF polypeptide are fused in-frame to each other. The non-BRAF polypeptide can be fused to the N-terminus or C-terminus of the BRAF polypeptide. For example, in one embodiment the fusion protein is a GST-BRAF fusion protein in which the BRAF sequences are fused to the C-terminus of the GST sequences. Such fusion proteins can facilitate the purification of recombinant BRAF proteins. In another embodiment, the fusion protein is a BRAF protein containing a heterologous signal sequence at its N-terminus. In certain host cells (e.g., mammalian host cells), expression and/or secretion of a BRAF protein can be increased through use of a heterologous signal sequence.

Preferably, a BRAF chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A BRAF-encoding nucleic acid can be cloned into such an expression vector such that the fusion moiety is linked in-frame to the BRAF protein.

In a preferred embodiment, the isolated BRAF polypeptides of the invention contain one or more mutations (e.g., substitutions or deletions) with respect to a wild-type BRAF polypeptide sequence. In one embodiment, the mutant BRAF polypeptides contain one or more mutations with respect to a human wild-type BRAF polypeptide sequence (SEQ ID NO:2). In a particularly preferred embodiment, the one or more mutations confer resistance to a BRAF inhibitor. In an exemplary embodiment, the BRAF inhibitor is RAF-265. A mutant BRAF protein of the invention exhibits a biological activity characteristic of a wild-type BRAF protein. Such a biological activity can include, for example, phosphorylation of MEK1 or MEK2. Exemplary mutant BRAF polypeptides of the invention include BRAF polypeptides comprising a mutation at one or more of the following amino acid residues with respect to the wild type human BRAF polypeptide: A29, H72, S113, S124, P162, C194, L227, P231, C251, V291, Q329, V483, L485, T521, V528, D587, P655, S657, S683, P686, C696, L697, P722, F738, or C748. Exemplary mutant BRAF polypeptides of the invention also include BRAF polypeptides comprising one or more of the following amino acid substitutions with respect to the wild type human BRAF protein: A29V, H72N, S113I, S124F, P162H, C194*, L227F, P231T, C251F, V291F, Q329K, V483E, L485F, T521K, V528F, D587E, P655T, S657*, S683R, P686Q, P686T, C696*, L697I, P722T, F738L, and C748F.

Mutant BRAF proteins can be generated by mutagenesis of a wild-type BRAF protein, or of the nucleic acid molecule encoding a wild-type BRAF protein. Mutant BRAF proteins can also be identified by screening combinatorial libraries of BRAF mutants for a mutant BRAF protein having a desired activity, e.g., resistance to a BRAF inhibitor. Several techniques are known in the art for screening gene products of combinatorial libraries made by point mutations or truncation, and for screening cDNA libraries for gene products having a selected property. Such techniques are adaptable for rapid screening of the gene libraries generated by combinatorial mutagenesis. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected.

VIII. Detection of Mutations

In another aspect, the invention pertains to methods of detecting the presence of a mutant BRAF protein in a sample (e.g., a biological sample from a cancer patient). A variety of screening methods can be used to detect the presence of a mutant BRAF protein of the invention in a sample, e.g., a nucleic acid and/or a polypeptide sample. In specific embodiments, the sample contains a cell or cell extract. In exemplary embodiments, the sample is obtained from a subject, e.g., a subject having cancer.

Methods for detecting the presence of resistance mutations in genomic DNA, cDNA, and RNA (i.e., mRNA) containing a sequence encoding a BRAF protein, or biologically active portion thereof, can be used within the scope of the present invention. Likewise, methods for detecting the presence of resistance mutations in BRAF polypeptides, or biologically active portions thereof, can be used within the scope of the present invention. In particular embodiments, methods including, but not limited to, the following can be used to detect the presence of a BRAF polypeptide, or a nucleic acid molecule encoding a BRAF polypeptide, having a mutation at one or more of the following amino acid residues: A29, H72, S113, S124, P162, C194, L227, P231, C251, V291, Q329, V483, L485, T521, V528, D587, P655, S657, S683, P686, C696, L697, P722, F738, or C748. In exemplary embodiments, methods including, but not limited to, the following can be used to detect the presence of a BRAF polypeptide, or a nucleic acid molecule encoding a BRAF polypeptide, having one or more of the following mutations: A29V, H72N, S113I, S124F, P162H, C194*, L227F, P231T, C251F, V291F, Q329K, V483E, L485F, T521K, V528F, D587E, P655T, S657*, S683R, P686Q, P686T, C696*, L697I, P722T, F738L, and C748F.

Point mutations can be detected using methods including denaturing gradient gel electrophoresis ("DGGE"), restriction fragment length polymorphism analysis ("RFLP"), chemical or enzymatic cleavage methods, direct sequencing of target regions amplified by PCR (see above), single-strand conformation polymorphism analysis ("SSCP"), polymerase chain reaction, sequencing, hybridization, "hybrid capture" followed by pyrosequencing or single-molecule sequencing, and other methods known in the art. One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations. U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase 1 in mismatch assays. For example, Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that can be used in the practice of the present invention are disclosed in U.S. Pat. Nos. 5,849,483, 5,851,770, 5,866,337, 5,925,525 and 5,928,870, each of which is incorporated herein by reference in its entirety.

Screening methods can be performed to screen an individual for the occurrence of the mutations identified above. For example, in one embodiment, a sample (such as blood or other bodily fluid or cell or tissue sample) is taken from a patient for genotype analysis. In an exemplary embodiment, the patient is a cancer patient. The presence or absence of one or more mutations described herein determines the ability of the screened individuals to resist therapy with a first-generation BRAF inhibitor. According to methods provided by the invention, these results will be used to adjust and/or alter the dose of the first-generation BRAF inhibitor, or to select a course of treatment using a second-generation BRAF inhibitor. Effective treatment of a subject having cancer can comprise the eradication of a cancer cell, the cessation or reduction of cancer (such as solid tumor) growth rate, or the amelioration of at least one cancer symptom.

The resistance mutations in BRAF polypeptides, or in nucleic acid molecules encoding BRAF polypeptides, can be detected using any suitable methods known in the art, or modifications thereof, including the methods described below. Such methods include the use of allele-specific polymerase chain reaction, direct or indirect sequencing of the site, the use of restriction enzymes where the respective alleles of the site create or destroy a restriction site, the use of allele-specific hybridization probes, the use of antibodies that are specific for mutant BRAF polypeptides, or any other biochemical interpretation.

1. DNA Sequencing

The most commonly used method of characterizing a mutation is direct DNA sequencing of the genetic locus that flanks and includes the polymorphism. Such analysis can be accomplished using either the "dideoxy-mediated chain termination method," also known as the "Sanger Method" (Sanger, F., et al., 1975) or the "chemical degradation method," also known as the "Maxam-Gilbert method" (Maxam, A. M., et al., 1977). Sequencing in combination with genomic sequence-specific amplification technologies, such as the polymerase chain reaction, can be utilized to facilitate the recovery of the desired genes (Mullis, K. et al., 1986; European Patent Appln. 50,424; European Patent Appln. 84,796, European Patent Application 258,017, European Patent Appln. 237,362; European Patent Appln. 201,184; U.S. Pat. Nos. 4,683,202; 4,582,788; and 4,683,194), all of which are incorporated herein by reference. Sequencing of pooled samples can also be accomplished using Solexa/Illumina sequencing (Illumina,® San Diego, Calif.), pyrosequencing, or other single-molecule sequencing approaches.

2. Exonuclease Resistance

Other methods that can be employed to determine the identity of a nucleotide present at a mutated site utilize a specialized exonuclease-resistant nucleotide derivative (U.S. Pat. No. 4,656,127). A primer complementary to an allelic sequence immediately 3'- to the polymorphic site is hybridized to the DNA under investigation. If the polymorphic site on the DNA contains a nucleotide that is complementary to the particular exonucleotide-resistant nucleotide derivative present, then that derivative will be incorporated by a polymerase onto the end of the hybridized primer. Such incorporation makes the primer resistant to exonuclease cleavage and thereby permits its detection. As the identity of the exonucleotide-resistant derivative is known, one can determine the specific nucleotide present in the polymorphic site of the DNA.

3. Microsequencing Methods

Several other primer-guided nucleotide incorporation procedures for assaying mutated sites in DNA have been described (Komher, J. S. et al., 1989; Sokolov, B. P., 1990; Syvanen 1990; Kuppuswamy et al., 1991; Prezant et al., 1992; Ugozzoll, L. et al., 1992; Nyren et al., 1993). These methods rely on the incorporation of labeled deoxynucleotides to discriminate between bases at a mutated site. As the signal is proportional to the number of deoxynucleotides incorporated, mutations that occur in runs of the same nucleotide result in a signal that is proportional to the length of the run (Syvanen et al., 1993).

4. Extension in Solution

French Patent 2,650,840 and PCT Application No. WO91/02087 discuss a solution-based method for determining the identity of the nucleotide of a mutated site. According to these methods, a primer complementary to allelic sequences immediately 3'- to a polymorphic site is used. The identity of the nucleotide of that site is determined using labeled dideoxynucleotide derivatives which are incorporated at the end of the primer if complementary to the nucleotide of the polymorphic site.

5. Genetic Bit Analysis or Solid-Phase Extension

PCT Appln. No. 92/15712 describes a method that uses mixtures of labeled terminators and a primer that is complementary to the sequence 3' to a polymorphic site. The labeled terminator that is incorporated is complementary to the nucleotide present in the polymorphic site of the target molecule being evaluated and is thus identified. Here, the primer or the target molecule is immobilized to a solid phase.

6. Oligonucleotide Ligation Assay (OLA)

Oligonucleotide Ligation Assay is a solid phase method that uses different methodology than that described above (Landegren et al., 1988). Two oligonucleotides capable of hybridizing to abutting sequences of a single strand of a target DNA are utilized. One of these oligonucleotides is biotinylated while the other is detectably labeled. If the precise complementary sequence is found in a target molecule, the oligonucleotides will hybridize such that their termini abut, and create a ligation substrate. Ligation permits the recovery of the labeled oligonucleotide using avidin. Other nucleic acid detection assays, based on this method, combined with PCR are also described (Nickerson et al., 1990). Here, PCR is used to achieve the exponential amplification of target DNA, which is then detected using the OLA.

7. Ligase/Polymerase-Mediated Genetic Bit Analysis

U.S. Pat. No. 5,952,174 describes a method that also involves two primers capable of hybridizing to abutting sequences of a target molecule. The hybridized product is formed on a solid support to which the target is immobilized. Here the hybridization occurs such that the primers are separated from one another by a space of a single nucleotide. Incubating this hybridized product in the presence of a polymerase, a ligase, and a nucleoside triphosphate mixture containing at least one deoxynucleoside triphosphate allows the ligation of any pair of abutting hybridized oligonucleotides. Addition of a ligase results in two events required to generate a signal, extension and ligation. This provides a higher specificity and lower "noise" than methods using either extension or ligation alone, and unlike the polymerase-based assays, this method enhances the specificity of the polymerase step by combining it with a second hybridization and a ligation step for a signal to be attached to the solid phase.

8. Methods of Nucleic Acid Transfer

For some methods of the present invention, methods of nucleic acid transfer can be employed. Suitable methods for nucleic acid delivery to effect expression of compositions of the present invention are believed to include virtually any method by which a nucleic acid (e.g., DNA, including viral and nonviral vectors) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by Agrobacterium-mediated transformation (U.S. Pat. Nos. 5,591,616 and 5,563,055, each incorporated herein by reference); by PEG-mediated transformation of protoplasts (Omirulleh et al., 1993; U.S. Pat. Nos. 4,684,611 and 4,952,500, each incorporated herein by reference); or by desiccation/inhibition-mediated DNA uptake (Potrykus et al., 1985). Through the application of techniques such as these, organelle(s), cell(s), tissue(s) or organism(s) can be stably or transiently transformed.

9. Allele-Specific Antibodies

BRAF polypeptides having one or more resistance mutations described herein can be detected using antibodies that specifically recognize the mutant BRAF polypeptides, but do not recognize wild-type BRAF polypeptides. Antibodies can be raised against one or more allelic forms of the BRAF polypeptides having one or more resistance mutations. Techniques for using a specific protein or an oligopeptide as an antigen to elicit antibodies that specifically recognize epitopes on the peptide or protein are well known. In one embodiment, the DNA sequence of the desired allelic form of the target gene can be cloned by insertion into an appropriate expression vector and translated into protein in a prokaryotic or eukaryotic host cell. The protein can be recovered and used as an antigen to elicit the production of specific antibodies. In another embodiment, the DNA of the desired allelic form of the target gene is amplified by PCR technology and is subsequently translated in vitro into protein to be used as the antigen to elicit the production of specific antibodies. A third embodiment is to use the DNA sequence of the alternative alleles as a basis for the generation of synthetic peptides representing the amino acid sequence of the alleles for use as antigen to elicit the production of specific antibodies.

Antibodies can be generated either by standard monoclonal antibody techniques or generated through recombinant based expression systems. See generally, Abbas, Lichtman, and Pober, Cellular and Molecular Immunology, W.B. Saunders Co. (1991). The term "antibodies" is meant to include intact antibody molecules as well as antibody fragments or derivatives, such as Fab and F(ab')2, which are capable of specifically binding to antigen. The antibodies so produced will preferentially bind only the mutant protein produced in the allelic form which was used as an antigen to create the antibody. Methods of generating allele-specific antibodies are also described in U.S. Pat. No. 6,200,754 and U.S. Pat. No. 6,054,273, the entire contents of which are incorporated herein by reference.

Such antibodies specific for mutant BRAF polypeptides can be used to detect the presence of a BRAF polypeptide having one or more resistance mutations in a sample, e.g., an assay sample, a cell sample, a cell extract, a biological sample, or a patient sample, using techniques known in the art. These techniques include, for example, Western blot, immunohistochemistry, indirect immunofluorescence, and antibody microarray. Antibodies which specifically recognize mutant BRAF polypeptides can also be second-generation BRAF inhibitors. The ability of an antibody which specifically recognizes a mutant BRAF polypeptide to inhibit the biological activity of the mutant BRAF polypeptide can be determined using the methods described herein for identifying second-generation BRAF inhibitors.

IX. Diagnostic and Screening Applications

The foregoing techniques can be used to determine the presence or absence of a previously identified resistance mutation in a BRAF nucleic acid or polypeptide molecule in a sample obtained from a patient. Identification of a mutant BRAF nucleic acid or polypeptide molecule in a patient sample can be useful for characterizing a disease or condition in the patient. For example, in a patient having a disease associated with aberrant expression or activation of BRAF (e.g., a cancer), identification of a mutant BRAF nucleic acid or polypeptide molecule in sample (e.g., a cancer-cell containing sample) obtained from the patient indicates that the patient is at a relatively high risk of relapse or lack of response to treatment with a BRAF inhibitor. In one embodiment, identification of a BRAF nucleic acid or polypeptide molecule containing one or more mutations described herein in a cancer-cell containing sample obtained from a patient indicates that the patient is at a relatively high risk of relapse or lack of response to treatment with a first generation BRAF inhibitor, e.g., RAF-265.

A patient who has a BRAF resistance mutation described herein has a higher risk of relapse from treatment with a first-generation BRAF inhibitor than a patient in whom a BRAF resistance mutation can not be detected. Accordingly, as used herein, the term "relatively high risk of relapse" is in relation to a patient in whom a mutant BRAF nucleic acid or polypeptide molecule cannot be detected. That is, a patient who has a "relatively high risk of relapse" is a patient who has a greater risk of relapse as compared to a patient in whom a mutant BRAF nucleic acid or polypeptide molecule cannot be detected.

In certain embodiments, identification of a BRAF polypeptide, or a nucleic acid encoding a BRAF polypeptide, having a mutation at one or more of the following residues indicates that the patient is at relatively high risk of relapse or lack of response to treatment with a first-generation BRAF inhibitor, e.g., RAF-265: A29, H72, S113, S124, P162, C194, L227, P231, C251, V291, Q329, V483, L485, T521, V528, D587, P655, S657, S683, P686, C696, L697, P722, F738, and C748. In exemplary embodiments, identification of a BRAF polypeptide, or a nucleic acid encoding a BRAF polypeptide, having one or more of the following resistance mutations indicates that the patient is at relatively high risk of relapse or lack of response to treatment with a BRAF inhibitor, e.g., RAF-265: A29V, H72N, S113I, S124F, P162H, C194*, L227F, P231T, C251F, V291F, Q329K, V483E, L485F, T521K, V528F, D587E, P655T, S657*, S683R, P686Q, P686T, C696*, L697I, P722T, F738L, or C748F.

Determining the presence or absence of a mutant BRAF nucleic acid or polypeptide molecule in a patient sample also allows for the selection of an optimized treatment regimen for the patient, or stratification of the patient to a certain treatment group. In one embodiment, a treatment regimen comprising treatment with a first-generation BRAF inhibitor is selected for a patient wherein a cancer cell-containing sample from the patient does not contain a mutant BRAF nucleic acid or polypeptide molecule. Such a patient can be stratified to a treatment regimen comprising a first-generation BRAF inhibitor. The BRAF inhibitor can be given to such a patient at a standard dosage, at standard dosing intervals.

In another embodiment, a treatment regimen comprising treatment without a BRAF inhibitor is selected for a patient wherein a cancer cell-containing sample from the patient contains a mutant BRAF nucleic acid or polypeptide molecule, e.g., a BRAF nucleic acid or polypeptide molecule containing one or more of the mutations described herein. Such a patient can be stratified to a treatment regimen that does not comprise a BRAF inhibitor.

In another embodiment, a treatment regimen comprising treatment with an elevated dosage of a first-generation BRAF inhibitor is selected for a patient wherein a cancer cell-containing sample from the patient contains a mutant BRAF nucleic acid or polypeptide molecule. Such a patient can be stratified to a treatment regimen comprising an elevated dosage of a first-generation BRAF inhibitor. In an exemplary aspect of the foregoing embodiments, the first-generation BRAF inhibitor is RAF-265.

In an alternative embodiment, identification of a mutant BRAF nucleic acid or polypeptide molecule in a cancer-cell containing sample obtained from a patient indicates that the patient is likely to respond to treatment with a second-generation BRAF inhibitor. Accordingly, in one embodiment, a treatment regimen comprising treatment with a second-generation BRAF inhibitor is selected for a patient wherein a cancer cell-containing sample from the patient contains a mutant BRAF nucleic acid or polypeptide molecule. Such a patient can be stratified to a treatment regimen comprising a second-generation BRAF inhibitor.

In particular aspects of the foregoing embodiments, the mutant BRAF polypeptide has a mutation at one or more of the following residues: A29, H72, S113, S124, P162, C194, L227, P231, C251, V291, Q329, V483, L485, T521, V528, D587, P655, S657, S683, P686, C696, L697, P722, F738, and C748. In exemplary embodiments, the mutant BRAF polypeptide has one or more of the following mutations: A29V, H72N, S113I, S124F, P162H, C194*, L227F, P231T, C251F, V291F, Q329K, V483E, L485F, T521K, V528F, D587E, P655T, S657*, S683R, P686Q, P686T, C696*, L697I, P722T, F738L, and C748F. In a preferred embodiment, a mutant BRAF nucleic acid molecule encodes a mutant BRAF polypeptide containing a mutation at one or more of the foregoing amino acid residues.

Accordingly, in one embodiment, the invention provides a method of optimizing treatment of a subject having cancer, comprising extracting nucleic acid from cells of the cancer; and sequencing a nucleic acid molecule encoding a BRAF polypeptide; wherein the presence of nucleotides that alter the identity of an amino acid residue at one or more amino acids of the encoded BRAF polypeptide relative to the amino acid at one or more positions selected from the group consisting of A29, H72, S113, S124, P162, C194, L227, P231, C251, V291, Q329, V483, L485, T521, V528, D587, P655, S657, S683, P686, C696, L697, P722, F738, and C748 of SEQ ID NO:2 or SEQ ID NO:4, indicates a need to treat the subject with a MEK inhibitor or a second-generation RAF inhibitor.

In another embodiment, the invention provides a method of optimizing treatment of a subject having cancer, comprising extracting nucleic acid from cells of the cancer; and subjecting the sample to PCR and identifying the nucleotide sequence of a nucleic acid molecule encoding a BRAF polypeptide; wherein the presence of nucleotides that alter the identity of an amino acid residue at one or more amino acid of the encoded BRAF polypeptide relative to the amino acid at one or more positions selected from the group consisting of A29, H72, S113, S124, P162, C194, L227, P231, C251, V291, Q329, V483, L485, T521, V528, D587, P655, S657, S683, P686, C696, L697, P722, F738, and C748 of SEQ ID NO:2 or SEQ ID NO:4, indicates a need to treat the subject with a MEK inhibitor or a second-generation RAF inhibitor.

In another embodiment, the invention provides a method of treating a subject having cancer, comprising extracting nucleic acid from cells of the cancer; sequencing a nucleic acid molecule encoding a BRAF polypeptide; and administering a MEK inhibitor or a second-generation BRAF inhibitor to the subject when the nucleic acid molecule contains nucleotides that alter the identity of an amino acid residue at one or more amino acids of the encoded BRAF polypeptide relative to the amino acid at one or more positions selected from the group consisting of A29, H72, S113, S124, P162, C194, L227, P231, C251, V291, Q329, V483, L485, T521, V528, D587, P655, S657, S683, P686, C696, L697, P722, F738, and C748 of SEQ ID NO:2 or SEQ ID NO:4.

In another embodiment, the invention provides a method of treating a subject having cancer, comprising extracting nucleic acid from cells of the cancer; subjecting the sample to PCR and identifying the nucleotide sequence of a nucleic acid molecule encoding a BRAF polypeptide; and administering a MEK inhibitor or a second-generation RAF inhibitor to the subject when the nucleic acid molecule contains nucleotides that alter the identity of an amino acid residue at one or more amino acids of the encoded BRAF polypeptide relative to the amino acid at one or more positions selected from the group consisting of A29, H72, S113, S124, P162, C194, L227, P231, C251, V291, Q329, V483, L485, T521, V528, D587, P655, S657, S683, P686, C696, L697, P722, F738, and C748 of SEQ ID NO:2 or SEQ ID NO:4.

In another embodiment, the invention provides a method of identifying a subject having cancer who is likely to benefit from treatment with a MEK inhibitor or a second-generation RAF inhibitor, comprising: assaying a nucleic acid sample obtained from the cancer for the presence of one or more mutations in a nucleic acid molecule encoding a BRAF polypeptide that alter the identity of one or more amino acid residues of the encoded BRAF polypeptide relative to the amino acid at one or more positions selected from the group consisting of A29, H72, S113, S124, P162, C194, L227, P231, C251, V291, Q329, V483, L485, T521, V528, D587, P655, S657, S683, P686, C696, L697, P722, F738, and C748 of SEQ ID NO:2 or SEQ ID NO:4; and correlating the presence of the one or more mutations in a nucleic acid molecule encoding a BRAF polypeptide with a subject who is likely to benefit from treatment with a MEK inhibitor or a second-generation RAF inhibitor.

In another embodiment, the invention provides a method of identifying a subject having cancer who is likely to benefit from treatment with a MEK inhibitor or a second-generation RAF inhibitor, comprising assaying a nucleic acid sample obtained from the cancer for the presence of one or more mutations in a nucleic acid molecule encoding a BRAF polypeptide that alter the identity of one or more amino acid residues of the encoded BRAF polypeptide relative to the amino acid at one or more positions selected from the group consisting of A29, H72, S113, S124, P162, C194, L227, P231, C251, V291, Q329, V483, L485, T521, V528, D587, P655, S657, S683, P686, C696, L697, P722, F738, and C748 of SEQ ID NO:2 or SEQ ID NO:4; and correlating the presence of the one or more mutations in a nucleic acid molecule encoding a BRAF polypeptide with a subject who is likely to benefit from treatment with a MEK inhibitor or a second-generation RAF inhibitor.

In various embodiments of the foregoing aspects, the MEK inhibitor is CI-1040, AZD6244, PD318088, PD98059, PD334581, RDEA119, 6-Methoxy-7-(3-morpholin-4-yl-propoxy)-4-(4-phenoxy-phenylamino)-quinoline-3-carbonitrile or 4-[3-Chloro-4-(1-methyl-1H-imidazol-2-ylsulfanyl)-phenylamino]-6-methoxy-7-(3-morpholin-4-yl-propoxy)-quinoline-3-carbonitrile, or combinations thereof.

In another embodiment, the invention provides a method of identifying a subject having cancer as having a high risk of relapse during treatment with a first-generation BRAF inhibitor, comprising extracting nucleic acid from cells of the cancer; and sequencing a nucleic acid molecule encoding a BRAF polypeptide;
wherein the presence of nucleotides that alter the identity of an amino acid residue at one or more amino acids of the encoded BRAF polypeptide relative to the amino acid at one or more positions selected from the group consisting of A29, H72, S113, S124, P162, C194, L227, P231, C251, V291, Q329, V483, L485, T521, V528, D587, P655, S657, S683, P686, C696, L697, P722, F738, and C748 of SEQ ID NO:2 or SEQ ID NO:4, identifies the subject as having a high risk of relapse during treatment with a first-generation BRAF inhibitor.

In another embodiment, the invention provides a method of identifying a subject having cancer as being unresponsive to treatment with a first-generation BRAF inhibitor, comprising extracting nucleic acid from cells of the cancer; and sequencing a nucleic acid molecule encoding a BRAF polypeptide; wherein the presence of nucleotides that alter the identity of an amino acid residue at one or more amino acids of the encoded BRAF polypeptide relative to the amino acid at one or more positions selected from the group consisting of A29, H72, S113, S124, P162, C194, L227, P231, C251, V291, Q329, V483, L485, T521, V528, D587, P655, S657, S683, P686, C696, L697, P722, F738, and C748 of SEQ ID NO:2 or SEQ ID NO:4, identifies the subject as being unresponsive to treatment with a first-generation BRAF inhibitor.

In various embodiments of the foregoing aspects, the RAF inhibitor is RAF265 or PLX 4720. In some embodiments of the foregoing aspects, the cancer is selected from the group consisting of leukemias, lymphomas, myelomas, carcinomas, metastatic carcinomas, sarcomas, adenomas, nervous system cancers and genitourinary cancers. In other embodiments, the cancer is melanoma.

X. Methods of Treatment

In various embodiments, the invention provides methods of treating a subject having a cancer. In exemplary embodiments, the subject has a cancer containing a BRAF polypeptide having one or more mutations, e.g., one or more of the resistance mutations described herein. In related embodiments, the subject has a cancer containing a nucleic acid molecule encoding a BRAF polypeptide having one or more mutations, e.g., one or more of the resistance mutations described herein. The term "treated," "treating" or "treatment" includes the diminishment or alleviation of at least one symptom associated with the condition being treated. For example, treatment can be diminishment of one or several symptoms of a disorder or complete eradication of a disorder, such as cancer. Likewise, a therapeutically effective amount of a compound is a quantity sufficient to diminish or alleviate at least one symptom associated with the conditions being treated.

Accordingly, in some embodiments, the invention provides methods of treating a subject having a cancer comprising administering to the subject a second-generation RAF inhibitor. In other embodiments, the invention provides methods of treating a subject having a cancer comprising administering to the subject a MEK inhibitor. In exemplary embodiments of the foregoing aspects, one or more mutations in a BRAF polypeptide, or in a nucleic acid molecule encoding a BRAF polypeptide were identified in the cancer, which confer resistance to one or more BRAF inhibitors as described herein. For example, the invention provides a method of treating a cancer containing amino acid substitutions at one or more of the following positions in BRAF, optionally in addition to having a BRAF mutation at V600E: A29, H72, S113, S124, P162, C194, L227, P231, C251, V291, Q329, V483, L485, T521, V528, D587, P655, S657, S683, P686, C696, L697, P722, F738, and C748 of SEQ ID NO:2 or SEQ ID NO:4, said method comprising administering to the subject a therapeutically effective amount of a second generation BRAF inhibitor. The invention further provides a method of treating a cancer containing amino acid substitutions at one or more of the following positions in BRAF, optionally in addition to having a BRAF mutation at V600E: A29, H72, S113, S124, P162, C194, L227, P231, C251, V291, Q329, V483, L485, T521, V528, D587, P655, S657, S683, P686, C696, L697, P722, F738, and C748 of SEQ ID NO:2 or SEQ ID NO:4, said method comprising administering to the subject a therapeutically effective amount of a MEK inhibitor. As MEK is activated downstream of RAF, a MEK inhibitor can successfully inhibit RAF signaling in cells having one or more of the RAF resistance mutations described herein.

MEK inhibitors suitable for practicing the invention include, but are not limited to, I-1040, AZD6244, PD318088, PD98059, PD334581, RDEA119, 6-Methoxy-7-(3-morpholin-4-yl-propoxy)-4-(4-phenoxy-phenylamino)-quinoline-3-carbonitrile, 4-[3-Chloro-4-(1-methyl-1H-imidazol-2-ylsulfanyl)-phenylamino]-6-methoxy-7-(3-morpholin-4-yl-propoxy)-quinoline-3-carbonitrile, and the Roche compound RG7420. Additional MEK inhibitors suitable for practicing the invention include, but are not limited to, the compounds described in WO 2008076415, US 20080166359, WO 2008067481, WO 2008055236, US 20080188453, US 20080058340, WO 2007014011, WO 2008024724, US 20080081821, WO 2008024725, US 20080085886, WO 2008021389, WO 2007123939, US 20070287709, WO 2007123936, US 20070287737, US 20070244164, WO 2007121481, US 20070238710, WO 2007121269, WO 2007096259, US 20070197617, WO 2007071951, EP 1966155, IN 2008MN01163, WO 2007044084, AU 2006299902, CA 2608201, EP 1922307, EP 1967516, MX 200714540, IN 2007DN09015, NO 2007006412, KR 2008019236, WO 2007044515, AU 2006302415, CA 2622755, EP 1934174, IN 2008DN02771, KR 2008050601, WO 2007025090, US 20070049591, WO 2007014011, AU 2006272837, CA 2618218, EP 1912636, US 20080058340, MX 200802114, KR 2008068637, US 20060194802, WO 2006133417, WO 2006058752, AU 2005311451, CA 2586796, EP 1828184, JP 2008521858, US 20070299103, NO 2007003393, WO 2006056427, AU 2005308956, CA 2587178, EP 1838675, JP 2008520615, NO 2007003259, US 20070293544, WO 2006045514, AU 2005298932, CA 2582247, EP 1802579, CN 101065358, JP 2008517024, IN 2007DN02762, MX 200704781, KR 2007067727, NO 2007002595, JP 2006083133, WO 2006029862, US 20060063814, U.S. Pat. No. 7,371,869, AU 2005284293, CA 2579130, EP 1791837, CN 101023079, JP 2008513397, BR 2005015371, KR 2007043895, MX 200703166, IN 2007CN01145, WO 2006024034, AU 2005276974, CA 2578283, US 20060079526, EP 1799656, CN 101044125, JP 2008510839, MX 200702208, IN 2007DN02041, WO 2006018188, AU 2005274390, CA 2576599, EP 1781649, CN 101006085, JP 2008509950, BR 2005014515, AT 404556, US 20060041146, MX 200701846, IN 2007CN00695, KR 2007034635, WO 2006011466, AU 2005265769, CA 2575232, EP 1780197, BR 2005013750, JP 4090070, MX 200700736, CN 101124199, KR 2007041752, IN 2007DN01319, WO 2005121142, AU 2005252110, CA 2569850, US 20060014768, U.S. Pat. No. 7,378,423, EP 1761528, CN 101006086, AT 383360, BR 2005011967, JP 2008501631, EP 1894932, ES 2297723, MX 2006PA14478, NO 2007000155, IN 2007CN00102, KR 2007034581, HK 1107084, JP 2008201788, US 20050256123, US 20050250782, US 20070112038, US 20050187247, WO 2005082891, WO 2005051302, AU 2004293019, CA 2546353, US 20050130943, US 20050130976, US 20050153942, EP 1689233, JP 2007511615, WO 2005051301 AU 2004293018, CA 2545660, US 20050130943, US 20050130976, US 20050153942, EP 1682138, BR 2004016692, CN 1905873, JP 2007511614, MX 2006PA05657, IN 2006DN03183, NO 2006002692, KR 2007026343, WO 2005028426, EP 1674452, US 20070105859, US 20050054701, U.S. Pat. No. 7,230,099, US 20050049419, U.S. Pat. No. 7,144,907, AU 2004270699, CA 2537321, WO 2005023759, EP 1673339, BR 2004014111, CN 1874769, JP 2007504241, JP 4131741, US 20060030610, MX 2006PA02466, NO 2006001506, US 20050049419, U.S. Pat. No. 7,144,907, US 20050054701, U.S. Pat. No. 7,230,099, AU 2004270699, CA 2537321, WO 2005023759, EP 1673339, BR 2004014111, CN 1874769, JP 2007504241, JP 4131741 US 20060030610, MX 2006PA02466, IN 2006DN01661, NO 2006001506, US 20060189808, US 20060189649, U.S. Pat. No. 7,271,178, US 20060189668, US 20050049276, WO 2005009975, CA 2532067, EP 1651214, BR 2004012851, JP 2006528621, US 20050026970, U.S. Pat. No. 7,160,915, MX 2006PA00921, WO 2005007616, US 20050059710, WO 2005000818, US 20050026964, U.S. Pat. No. 7,273,877, WO 2004056789, US 20050004186, CA 2509405, AU 2003286306, EP 1578736, BR 2003017254, JP 2006516967, MX 2005PA06803, WO 2004044219, AU 2003291268, WO 2004041811, AU 2003278369, EP 1575943, JP 2006508944, US 20050282856, U.S. Pat. No. 7,173,136, US 20070191346, WO 2004041185, AU 2003287366, US 20060270643, WO 2004030620, AU 2003275282, US 20040092514, U.S. Pat. No. 7,232,826, EP 1545529, US 20040039037, U.S. Pat. No. 6,989,451, WO 2003077855, CA 2478534, AU 2003220202, US 20030216460, EP 1482944, CN 1652792, JP 2005526076, RU 2300528, BR 2003006016, MX 2004PA08894, US 20060106225, WO 2003062191, CA 2473545, EP 1467968, BR 2003007060, JP 2005515253, TW 592692, US 20040006245, U.S. Pat. No. 6,891,066, MX 2004PA05527, US 20050137263, U.S. Pat. No. 7,078,438, WO 2003062189, CA 2472367, EP 1467965, BR 2003007071, JP 2005515251, US 20030232889, U.S. Pat. No. 6,770,778, MX 2004PA05528, WO 2003047585, AU 2002347360, WO 2003047583, AU 2002365665, WO 2003047523, CA 2466762, AU 2002365899, US 20030125359, U.S. Pat. No. 7,307,071, JP 2005526008, EP 1578346, WO 2003035626, CA 2463101, AU 2002359291, EP 1438295, JP 2005508972, US 20050054706, U.S. Pat. No. 7,253,199, US 20070293555, AU 2008202731, U.S. Pat. No. 6,506,798, WO 9901421, WO 2000041994, U.S. Pat. No. 6,310,060, WO 2002006213, CA 2416685, AU 2001073498, BR 2001012584, HU 2003002781, JP 2004504294, JP 3811775, EE 200300030, NZ 524120, AU 2001273498, IN 2003MN00028, NO 2003000249, KR 773621, MX 2003PA00591, HR 2003000083, BG 107564, ZA 2003000348, US 20040054172, U.S. Pat. No. 6,960,614, HK 1055943, US 20050176820, U.S. Pat. No. 7,411,001, WO 2000042029, JP 2000204077, CA 2355374, EP 1144394, BR 9916896, TR 200102029, HU 2001005092, JP 2002534515, EE 200100374, NZ 513432, AT 302761, ES 2249060, ZA 2001005219, MX 2001PA06659, IN 2001MN00785, NO 2001003451, HR 2001000525, BG 105801, U.S. Pat. No. 6,545,030, HK 1042488, US 20030004193, WO 2000042022, JP 2000204079, CA 2355470, EP 1144385, BR 9916904, TR 200102030, HU 2001005113, EE 200100373, JP 2002534510, NZ 513433, AT 302193, ES 2247859, MX 2001PA06568, ZA 2001005224, IN 2001MN00786, U.S. Pat. No. 6,469,004, NO 2001003452, HR 2001000524, BG 105800, WO 2000042003, JP 2000212157, CA 2349832, EP 1144371, BR 9916885, AT 309205, ES 2252996, MX 2001PA04332, U.S. Pat. No. 6,440,966, US 20030092748, U.S. Pat. No. 6,750,217, WO 2000042002, JP 2000204075, CA 2349467, EP 1144372, BR 9916894, JP 2002534497, AT 311363, ES 2251851, MX 2001PA04331, U.S. Pat. No. 6,455,582, US 20030045521, U.S. Pat. No. 6,835,749, WO 2000037141, CA 2352326, BR 9916839, EP 1140291, TR 200101871, HU 2001004844, JP 2002532570, EE 200100339, NZ 512859, AT 310567, ES2253928, ZA 2001004277, MX 2001PA05476, IN 2001MN00673, NO 2001003099, HR 2001000473, BG 105715, US 20040171632, GB 2323845, WO 9901426, CA 2290506, AU 9882627, AU 757046, EP 993439, BR 9810366, NZ 501276, HU 2000003731, JP 2002511092, AT 277895, IL 132840, PT 993439, ES 2229515, TW 396149, ZA 9805728, MX 9910649, NO 9906491, NO 315271, US 20030078428, U.S. Pat. No. 6,821,963, US 20050049429, US 20060052608, U.S. Pat. No. 7,169,816, WO 9901421, CA 2290509, AU 9882626, AU 756586, EP 993437, BR 9810385, JP 2002509536, NZ 501277, AT 344791, ES 2274572, TW 221831, ZA 9805726, MX 9910556, U.S. Pat. No. 6,310,060, U.S. Pat. No. 6,506,798, US 20020022647, U.S. Pat. No. 6,492,363, US 20030149015, and U.S. Pat. No. 7,019,033, the entire contents of which are incorporated herein by reference. Dosages, formulations, and modes of administration of the foregoing compounds are known in the art. Exemplary modes of administration include, but are not limited to, oral, subcutaneous, intravenous, or parenteral. Liquid dosage forms for oral administration can include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), cremaphor, glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinyl pyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof, and (j) dissolution rate enhancers like high molecular weight polyethylene glycols or polyvinyl pyrrolidone in physical mixtures or in form of solid dispersions. In the case of capsules, tablets and pills, the dosage form may also comprise buffering agents.

Because mutations in BRAF broadly enhance resistance in a number of types of cancer, the methods and second-generation BRAF inhibitors described herein are useful in treating a broad spectrum of cancers, including solid tumors and hematological malignancies. Examples of such tumors include but are not limited to leukemias, lymphomas, myelomas, carcinomas, metastatic carcinomas, sarcomas, adenomas, nervous system cancers and genitourinary cancers. In exemplary embodiments, the foregoing methods are useful in treating adult and pediatric acute lymphoblastic leukemia, acute myeloid leukemia, adrenocortical carcinoma, AIDS-related cancers, anal cancer, cancer of the appendix, astrocytoma, basal cell carcinoma, bile duct cancer, bladder cancer, bone cancer, osteosarcoma, fibrous histiocytoma, brain cancer, brain stem glioma, cerebellar astrocytoma, malignant glioma, ependymoma, medulloblastoma, supratentorial primitive neuroectodermal tumors, hypothalamic glioma, breast cancer, male breast cancer, bronchial adenomas, Burkitt lymphoma, carcinoid tumor, carcinoma of unknown origin, central nervous system lymphoma, cerebellar astrocytoma, malignant glioma, cervical cancer, childhood cancers, chronic lymphocytic leukemia, chronic myelogenous leukemia, chronic myeloproliferative disorders, colorectal cancer, cutaneous T-cell lymphoma, endometrial cancer, ependymoma, esophageal cancer, Ewing family tumors, extracranial germ cell tumor, extragonadal germ cell tumor, extrahepatic bile duct cancer, intraocular melanoma, retinoblastoma, gallbladder cancer, gastric cancer, gastrointestinal stromal tumor, extracranial germ cell tumor, extragonadal germ cell tumor, ovarian germ cell tumor, gestational trophoblastic tumor, glioma, hairy cell leukemia, head and neck cancer, hepatocellular cancer, Hodgkin lymphoma, non-Hodgkin lymphoma, hypopharyngeal cancer, hypothalamic and visual pathway glioma, islet cell tumors, Kaposi sarcoma, kidney cancer, renal cell cancer, laryngeal cancer, lip and oral cavity cancer, small cell lung cancer, non-small cell lung cancer, primary central nervous system lymphoma, Waldenstrom macroglobulinemia, malignant fibrous histiocytoma, medulloblastoma, melanoma, Merkel cell carcinoma, malignant mesothelioma, squamous neck cancer, multiple endocrine neoplasia syndrome, multiple myeloma, mycosis fungoides, myelodysplastic syndromes, myeloproliferative disorders, chronic myeloproliferative disorders, nasal cavity and paranasal sinus cancer, nasopharyngeal cancer, neuroblastoma, oropharyngeal cancer, ovarian cancer, pancreatic cancer, parathyroid cancer, penile cancer, pharyngeal cancer, pheochromocytoma, pineoblastoma and supratentorial primitive neuroectodermal tumors, pituitary cancer, plasma cell neoplasms, pleuropulmonary blastoma, prostate cancer, rectal cancer, rhabdomyosarcoma, salivary gland cancer, soft tissue sarcoma, uterine sarcoma, Sezary syndrome, non-melanoma skin cancer, small intestine cancer, squamous cell carcinoma, squamous neck cancer, supratentorial primitive neuroectodermal tumors, testicular cancer, throat cancer, thymoma and thymic carcinoma, thyroid cancer, transitional cell cancer, trophoblastic tumors, urethral cancer, uterine cancer, uterine sarcoma, vaginal cancer, vulvar cancer, and Wilms tumor.

XI. Kits

Various kits may be assembled as part of the present invention. A kit can contain components to assay for mutations in BRAF to evaluate a particular patient for the risk of developing resistance to therapy using a BRAF inhibitor, and thus allow a clinician to determine whether an alternative treatment for the patient is needed. Such kits can contain reagents that allow for mutations to be evaluated, such as primer sets to evaluate mutations correlated with relevant phenotypic manifestations concerning resistance to a BRAF inhibitor (e.g., RAF-265). It is contemplated that primers (or pairs of primers) that are complementary to or identical to all or part of SEQ ID NO:1, for example, can be part of a kit. In preferred embodiments, the primers can be used to specifically detect or amplify a nucleic acid molecule encoding a mutant BRAF polypeptide containing a mutation at one or more of the following amino acid residues: A29, H72, S113, S124, P162, C194, L227, P231, C251, V291, Q329, V483, L485, T521, V528, D587, P655, S657, S683, P686, C696, L697, P722, F738, and C748. In exemplary embodiments, the primers specifically detect or amplify a nucleic acid molecule encoding a BRAF polypeptide containing one or more of the following mutations: A29V, H72N, S113I, S124F, P162H, C194*, L227F, P231T, C251F, V291F, Q329K, V483E, L485F, T521K, V528F, D587E, P655T, S657*, S683R, P686Q, P686T, C696*, L697I, P722T, F738L, and C748F. In other embodiments, the kits contain instructions for using primers that are complementary or identical to all or part of SEQ ID NO:1 to amplify a nucleotide sequence encoding a BRAF polypeptide.

In other embodiments, the kits comprise compositions for detecting a mutation comprising a BRAF polypeptide, such as an antibody which specifically recognizes a mutant BRAF polypeptide containing one or more resistance mutations. Exemplary polypeptides include a mutant BRAF polypeptide containing a mutation at one or more of the following amino acid residues: A29, H72, S113, S124, P162, C194, L227, P231, C251, V291, Q329, V483, L485, T521, V528, D587, P655, S657, S683, P686, C696, L697, P722, F738, and C748. In other embodiments, the mutant BRAF polypeptide contains one or more of the following mutations: A29V, H72N, S113I, S124F, P162H, C194*, L227F, P231T, C251F, V291F, Q329K, V483E, L485F, T521K, V528F, D587E, P655T, S657*, S683R, P686Q, P686T, C696*, L697I, P722T, F738L, and C748F.

All of the essential materials and reagents required for assaying for BRAF mutations by a particular method discussed above can also be assembled together in a kit. When the components of the kit are provided in one or more liquid solutions, the liquid solution preferably is an aqueous solution, with a sterile aqueous solution being particularly preferred.

The components of the kit can also be provided in dried or lyophilized forms. When reagents or components are provided as a dried form, reconstitution generally is by the addition of a suitable solvent. It is envisioned that the solvent also can be provided in another container means.

The kits of the present invention also will typically include a means for containing the vials in close confinement for commercial sale such as, e.g., injection or blow-molded plastic containers into which the desired vials are retained. Irrespective of the number or type of containers, the kits of the invention also can comprise, or be packaged with, an instrument for assisting with sample collection and evaluation. Such an instrument can be an inhalant, syringe, pipette, forceps, measured spoon, eye dropper or any such medically approved delivery vehicle, for example.

The kits of the invention can also include an instruction sheet outlining suggested alternative therapies when particular mutations are identified in a patient. For example, an instruction sheet included with the kits of the invention can recommend that a patient having a disorder, e.g., a cancer, in which a mutant BRAF polypeptide has been identified, discontinue treatment with a first-generation BRAF inhibitor, be monitored for relapse during treatment with a first-generation BRAF inhibitor, continue treatment with a first-generation BRAF inhibitor at an elevated dosage, or initiate treatment with a second-generation BRAF inhibitor. An instruction sheet included with the kits of the invention can likewise recommend that a patient having a disorder in which a mutant BRAF polypeptide is not detectable continue treatment with a first-generation BRAF inhibitor at a standard dosage. In exemplary embodiments, the first-generation BRAF inhibitor is RAF-265.

This invention is further illustrated by the following examples, which should not be construed as limiting. The contents of all references, patents and published patent applications cited throughout this application are incorporated herein by reference.

EXAMPLES

Example 1

BRAF-V600E Random Mutagenesis Screen (RAF265 and PLX4720)

Generation of mutagenized libraries was accomplished using a modification of published methods. Briefly, mutagenesis was performed by propagating a BRAF(V600E) expression plasmid (pWZL-Blast-BRAF(V600E)) in *E. coli* deficient for the MutS, MutD5- and MutT-DNA repair genes (XL1-Red; Stratagene). Plasmid DNA was extracted from these bacteria and amplified in XL1-Blue *E. coli* (Stratagene). The mutagenized BRAF(V600E) plasmid or non-mutagenized control was used to infect A375 melanoma cells. After selection with blasticidin, cells were plated on 15-cm dishes and cultured in the presence of RAF inhibitors (RAF265 or PLX4720; 2 µM or 1.5 µM respectively) for 5 weeks until resistant clones emerged. Resistant clones were sequenced to identify mutations that occurred with high frequency. Results are shown in FIG. 5 (RAF265 screen) and FIG. 6 (PLX4720 screen). FIG. 7 depicts the locations of three BRAF mutations that arose with high frequency in both screens.

Example 2

Western Blot Analysis of pMEK1/2 and pERK1/2 Activation in Cells Containing BRAF Mutants 293T cells were transfected with 6 µg of pWZL(BLAST)-BRAF for each putative resistance allele and subsequently treated with a range of concentrations of the BRAF(V600E) inhibitor PLX4720 (0, 0.08, 0.4, 2, 5 and 10 µM) for 16 hours. Immunoblot studies were performed using standard procedures. Briefly, the treated cells were lysed with TNN buffer containing protease inhibitor (Roche), NaF and $NaVO_3$ (1 mM each). Lysates were quantified (Bradford assay), denatured (95° C.), and resolved by SDS gel electrophoresis. Proteins was transferred to nitrocellulose membranes and probed with primary antibodies recognizing BRAF (Santa Cruz; 1:10,000 dilution), p-ERK1/2, p-MEK1/2 (Ser-217/221), and α-tubulin (Cell Signaling Technology; 1:1,000 dilution). After incubation with the appropriate secondary antibody (anti-rabbit or anti-mouse IgG, HRP-linked; 1:1,000 dilution) (Cell Signaling Technology), proteins were detected using chemiluminescence (Pierce). Results are shown in FIG. 8. As shown therein, levels of phosphorylated MEK1/2 and ERK1/2 are increased in cells containing BRAF-V600E, BRAF-V600E-T521K, and BRAF V600E-P686Q. The increase in phosphorylated MEK1/2 and ERK1/2 is sustained in BRAF-V600E-T521K and BRAF V600E-P686Q cells in the presence of increasing concentrations of PLX4720.

Example 3

BRAF Kinase Assay 293T cells (70% confluent) were transfected with 15 µg pc-DNA-DEST40 containing BRAF(V600E) putative resistance alleles, kinase-dead BRAF, or wild-type. At 48 h postinfection, lysates were generated by standard methods. Pulldown using cobalt beads was performed for 30 min at 4° C. on 1 mg of whole cell extract. The protein-bound cobalt beads where incubated with 20 µL ATP/magnesium mixture (20 mM Mops pH 7.2, 25 mM β-glycerophosphate, 5 mM EGTA, 1 mM Na3VO4, 1 mM DTT, 75 mM MgCl2, and 0.5 mM ATP), 20 µL of dilution buffer (20 mM Mops, pH 7.2, 25 mM β-glycerol phosphate, 5 mM EGTA, 1 mM sodium orthovanadate, 1 mM DTT), and 1 µg of inactive MEK1 (obtained from Millipore) for 30 min at 30° C. The phosphorylated MEK1 product was detected by immunostaining using a p-MEK1/2 antibody (Cell Signaling Technology).

EQUIVALENTS

The invention has been described herein with reference to certain examples and embodiments only. No effort has been made to exhaustively describe all possible examples and embodiments of the invention. Indeed, those of skill in the art will appreciate that various additions, deletions, modifications and other changes can be made to the above-described examples and embodiments, without departing from the intended spirit and scope of the invention as recited in the following claims. It is intended that all such additions, deletions, modifications and other changes be included within the scope of the following claims.

What is claimed is:

1. A method of detecting a BRAF mutation in a subject having a cancer selected from: melanoma, colon carcinoma or thyroid carcinoma, the method comprising
   (a) obtaining a cancer cell-containing sample from the subject; and
   (b) performing a nucleic acid-based assay to analyze a nucleic acid molecule encoding a BRAF polypeptide for one or more mutations with respect to a nucleic acid molecule encoding a wild-type BRAF polypeptide (SEQ ID NO: 1) or a BRAF V600E polypeptide (SEQ ID NO: 3); and
   (c) detecting in the assay the one or more mutations occurring at positions encoding one or more amino acids in the BRAF polypeptide selected from the group consisting of A29, H72, SI13, S124, P162, C194, L227, P231, C251, V291, Q329, V483, L485, T521, V528, D587, P655, S657, S683, P686, C696, L697, P722, F738, and C748.

2. The method of claim 1, wherein the nucleic acid molecule encodes a BRAF polypeptide having one or more amino acid substitutions with respect to a wild type BRAF polypeptide (SEQ ID NO:2) or a BRAF V600E polypeptide (SEQ ID NO:4) selected from the group consisting of A29V, H72N, SI 131, S124F, P162H, C194*, L227F, P231T, C251F, V291F, Q329K, V483E, L485F, T521K, V528F, D587E, P655T, S657*, S683R, P686Q, P686T, C696*, L697I, P722T, F738L, and C748F.

3. The method of claim 1, wherein the mutant BRAF polypeptide is a BRAF polypeptide comprising a substitution at one or more of amino acid positions T521, V528, or P686.

4. The method of claim 1, wherein the mutant BRAF polypeptide is a BRAF polypeptide comprising a substitution at one or more of amino acid positions T521K, V528F, or P686Q.

5. The method of claim 1, wherein the presence of the one or more mutations in the nucleic acid molecule in the cancer cell-containing sample confers resistance to a RAF inhibitor selected from the group consisting of RAF-265 and PLX4720.

6. The method of claim 5, wherein the BRAF inhibitor is RAF-265.

7. The method of claim 5, wherein the RAF inhibitor is PLX4720.

8. The method of claim 1, wherein the cancer is melanoma.

* * * * *